US010064921B2

(12) United States Patent
Blumenfeld

(10) Patent No.: US 10,064,921 B2
(45) Date of Patent: *Sep. 4, 2018

(54) BOTULINUM TOXIN TREATMENTS OF NEUROLOGICAL AND NEUROPSYCHIATRIC DISORDERS

(71) Applicant: Allergan, Inc., Irvine, CA (US)

(72) Inventor: Andrew M. Blumenfeld, Del Mar, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/447,770

(22) Filed: Mar. 2, 2017

(65) Prior Publication Data

US 2017/0173123 A1 Jun. 22, 2017

Related U.S. Application Data

(63) Continuation of application No. 14/247,469, filed on Apr. 8, 2014, now abandoned, which is a continuation of application No. 10/964,898, filed on Oct. 12, 2004, now Pat. No. 8,734,810.

(60) Provisional application No. 60/574,967, filed on May 27, 2004, provisional application No. 60/556,150, filed on Mar. 24, 2004, provisional application No. 60/515,362, filed on Oct. 29, 2003.

(51) Int. Cl.
*A61K 38/48* (2006.01)
*A61K 9/00* (2006.01)

(52) U.S. Cl.
CPC ........ *A61K 38/4893* (2013.01); *A61K 9/0019* (2013.01); *A61K 9/0024* (2013.01); *C12Y 304/24069* (2013.01)

(58) Field of Classification Search
CPC .................. A61K 38/4893; A61K 9/24; C12Y 304/24069
See application file for complete search history.

(56) References Cited

U.S. PATENT DOCUMENTS

| | | | |
|---|---|---|---|
| 4,883,666 A | 11/1989 | Sabel et al. ................... 424/422 |
| 5,427,291 A | 6/1995 | Smith | |
| 5,674,205 A | 10/1997 | Pasricha et al. | |
| 5,714,468 A | 2/1998 | Binder | |
| 5,978,702 A | 11/1999 | Ward et al. | |
| 6,094,598 A | 7/2000 | Elsberry et al. .............. 607/116 |
| 6,113,915 A | 9/2000 | Aoki et al. | |
| 6,143,306 A | 11/2000 | Donovan | |
| 6,265,379 B1 | 7/2001 | Donovan | |
| 6,290,961 B1 | 9/2001 | Aoki et al. | |
| 6,306,403 B1 | 10/2001 | Donovan | |
| 6,328,977 B1 | 12/2001 | Donovan | |
| 6,358,513 B1 | 3/2002 | Voet et al. | |
| 6,365,164 B1 | 4/2002 | Schmidt | |
| 6,395,277 B1 | 5/2002 | Graham | |
| 6,620,415 B2 | 9/2003 | Donovan ................... 424/239.1 |
| 234,727 A1 | 12/2003 | Perlman ...................... 340/573.1 |
| 6,689,816 B2 | 2/2004 | Fogel ............................. 514/702 |
| 157,926 A1 | 8/2004 | Heresco-Levy et al. ..... 514/561 |
| 6,955,813 B2 | 10/2005 | Brooks et al. ............. 424/239.1 |
| 286,127 A1 | 12/2006 | Van Schaack et al. ..... 424/239.1 |
| 8,691,769 B2 | 3/2014 | Borodic et al. | |
| 2001/0012828 A1 | 8/2001 | Aoki et al. ......................... 514/2 |
| 2001/0053370 A1 | 12/2001 | Donovan ................... 424/239.1 |
| 2002/0176872 A1 | 11/2002 | Aoki et al. ................. 424/247.1 |
| 2002/0192239 A1 | 12/2002 | Borodic et al. | |
| 2003/0054975 A1 | 3/2003 | Voet ................................. 514/2 |
| 2004/0138097 A1* | 7/2004 | Guyuron ............ A61K 38/4886 128/898 |

FOREIGN PATENT DOCUMENTS

| | | | | |
|---|---|---|---|---|
| DE | 101 50 415 A1 | 10/2001 | ............ A61K 35/70 |
| EP | 0 605 501 B1 | 9/1992 | |
| WO | WO 95/17904 | 7/1995 | |
| WO | WO1996-33273 A1 | 10/1996 | |
| WO | WO 97/20579 | 6/1997 | |
| WO | WO 00/15245 | 9/1998 | ............ A61K 38/16 |
| WO | WO 00/07652 | 2/2000 | |
| WO | WO 03/094955 | 4/2003 | ............ A61K 38/48 |

OTHER PUBLICATIONS

Butler et al. Post-traumatic Stress Reactions Following Motor Vehicle Accidents. Am Fam Physician. Aug. 1, 1999;60(2):524-530.*
Sheftell et al. Migraine and psychiatric comorbidity: from theory and hypotheses to clinical application. Headache. Oct. 2002;42(9):934-44.*
U.S. Appl. No. 10/423,384, Ackerman, Alan H., filed Apr. 25, 2003.
U.S. Appl. No. 10/423,778, Ackerman, Alan H., filed Apr. 25, 2003.
U.S. Appl. No. 10/424,009, Ackerman, Alan H., filed Apr. 25, 2003.
U.S. Appl. No. 10/424,050, Ackerman, Alan H., filed Apr. 25, 2003.
Aguilera, Jose et al., *Stereotaxic Injection of Tetanus Toxin in Rat Central Nervous System Causes Alteration in Normal Levels of Monoamines*, Journal of Neurochemistry, vol. 56, No. 3, 1991, pp. 733-738.
Ahn et al., Plast. Reconstr. Surg. 105, 2002, pp. 778-784, abstract.
Auchus, Alexander et al., Agitated Behavior Relieved Folowing Treatment of Cervical Dystonia in Dementia, Neurology, 1995, 393, 45.
Aoki, K.R et al., *A Preclinical Comparison of the Local Muscle Weakening Efficacy, Safety, and Antigenic Potential of Botulinum Neurotoxin Serotypes A, B, and F*, Neurology 54, Apr. 2000 (Suppl 3).
Aoki, K.R. et al., *Botulinum toxin type A and other botulinum toxin serotypes: a comparative review of biochemical and pharmacological actions*; European Journal Neurology; 2001; 8 (Suppl 5):pp. 21-29.

(Continued)

*Primary Examiner* — Gregory S Emch
(74) *Attorney, Agent, or Firm* — Brigitte C. Phan; Ted A. Chan

(57) ABSTRACT

Methods for preventing or treating neuropsychiatric disorder and/or a neurological disorder including a neurological disorder mediated by the thalamus. Neuropsychiatric disorders and/or a neurological disorders, including a thalamically mediated disorder can be treated by peripheral administration of a botulinum toxin to or to the vicinity of a trigeminal sensory nerve, thereby preventing or treating a neurological disorder and/or a neuropsychiatric disorder.

15 Claims, 2 Drawing Sheets

(56) References Cited

OTHER PUBLICATIONS

Aoki, K.R.; *Physiology and Pharmacology of Therapeutic Botulinum Neurotoxins*; In: Kreyden OP, ed. Hyperhidrosis and Botulinum Toxin in Dermatology; Current Problems in Dermatology: Basel, Karger; 2002; 30: pp. 107-116.
Arezzo et al., Pain Med. 2:239, #202, Sep. 2001, abstract.
Ashby, P. et al., *Immediate Motor Effects of Stimulation through Electrodes Implanted in the Human Globus Pallidus*, Stereostatic and Functional Neurosurgery 70, 1998, pp. 1-18.
Ashby, P. et al.,*Motor effects of stimulating the human cerebellar thalamus*, Journal of Physiology 489.1, 1995, pp. 287-298.
Awad et al., J. Child. Neurol. 1999, 14, pp. 316-319.
Barnes, Deborah M., *Debate About Epilepsy: What Initiates Seizures?* Science 86, Nov. 21, 1986, vol. 234, pp. 938-941.
Bejjani, Boulos-Paul, et al., *Bilateral subthalmic stimulation for Parkinson's Disease by Using Three-Dimensional Stereostatic Magnetic Resonance Imaging and Electrophysiological Guidance*, J. Neurosurg. 92, 2000, pp. 615-625.
Bellezza, David M., et al., *Stereotactic Interstitial Brachytherapy*, Textbook of Stereotactic and Functional Neurosurgery, Edited by Gildenberg et al., McGraw-Hill Publ., Chapter 66, pp. 577-580.
Benabid, Alim L., et al,. *Deep brain stimulation of the corpus luysi (subthalamic nucleus) and other targets in Parkinson's disease. Extension to new indications such as dystonia and epilepsy*, J Neurol 248, 2001, Suppl. 3, pp. 111/37-111/47.
Berardelli et al., Ital. J. Neurol. Sci. 18, 1997, pp. 261-269.
Berman, Robert M., et al., *A Randomized Clinical Trial of Repetitive Transcranial Magnetic Stimulation in the Treatment of Major Depression*, Biological Psychiatry 47, 2000, pp. 332-337.
Berquist, Filip et al., *Evidence for different exocytosis pathways in dendritic and terminal dopamine release in vivo*, Brain Research 950, 2002, pp. 245-253.
Billet, Sara, et al., *Cholinergic Projections to the Visual Thalamus and Superior Collicullus*, Brain Research 847, 1999, pp. 121-123.
Boltzmann, Ludwig, *Post mortem studies in Parkinson's disease—is it possible to detect brain areas for specific syndromes?* J. Neural Transm, 1999, Suppl 56, pp. 1-29.
Brem, Henry, et al., *The safety of interstitial chemotherapy with BCNU-loaded polymer followed by radiation therapy in the treatment of newly diagnosed malignant gliomas, phase 1 trial*, Journal of Neuro-Oncology 26, 1995, pp. 111-123.
Brin, Mitchell F. et al., *Botulinum Toxin Type A: Pharmacology*, In: Mayer Nathaniel H, ed. Spasticity: Etiology, Evaluation, Management and the Role of Botulinum Toxin; 2002; pp. 110-124.
Brophy, B.P., et al., *Thalamotomy for Parkinsonian Tremor*, Stereotact Funct Neurosurg 69, 1997, pp. 1-4.
Callaway et al., Sem. Cutan. Med. Surg. Jun. 20, 2001, pp. 127-136.
Canafoglia, Laura, et al., *Rhythmic Cortical Myoclonus in a Case of HIV-Related Encephalopathy*, Mov Disord, vol. 18, No. 12, 2003.
Chappell, Phillip et al., *Future Therapies of Tourette Syndrome*; Neurol Clin; 1997; vol. 15, No. 2, May; pp. 429-450.
Cmelak, Anthony J. et al.; Low-dose stereotactic radiosurgery is inadequate for medically intractable mesial temporal lobe epilepsy: a case report; *Seizure*; 2001, 10, pp. 442-446.
Czaplinski, A., et al., *Tic Syndrome*, (article in Polish), Neurol. Neurochir. Pol. Nov.-Dec. 2002, 36(6), pp. 1251-1253.
Dabrowski et al., Dev. Med. Child Neurol 47, 2005, pp. 636-639.
Danober, Neuroscience 69, 1995, pp. 1183-1193.
Davis, Karen D., et al., *Globus pallidus stimulation activates the cortical motor system during alleviation of Parkinsonian symptoms*, Nature Medicine, vol. 3, No. 6, Jun. 1977, pp. 671-674.
*Diagnostic and Statistical Manual of Mental Disorders* 4th Ed.; Published by the American Psychiatric Association Washington, D.C.; pp. 108-116.
Dichter, Marc A.; Basic Mechanisms of Epilepsy: Targets for Therapeutic Intervention; *Epilepsia*. vol. 38, Suppl. 9, 1997, pp. S2-S6.
Dykstra, Dennis D. et al.; Treatment of Detrusor-Sphincter Dyssynergia with Botulinum A Toxin: A Double-Blind Study; *Arch Phys Med Rehabil*; Jan. 1990, 71, pp. 24-26.

Ferrari, David M. et al., *The protein disulphide-isomerase family: unravelling a string of folds*; Biochem J; 1999 (339) pp. 1-10.
Frankel et al., Neurology 36, 1986, pp. 378-382.
Fried, Itzhak et al.; Cerebral microdialysis combined with single-neuron and electroencephalographic recording in neurosurgical patients; *J Neurosurg* 91, 1999, pp. 697-705.
Galarreta, Mario et al.; Frequency-dependent synaptic depression and the balance of excitation and inhibition in the neocortex; *Nature Neuroscience*; vol. 1 No. 7, Nov. 1998, pp. 587-594.
Gale, Karen; Focal trigger zones and pathways of propagation in seizure generation. *Epilepsy: models, mechanism and concepts*; Schwartzkroin, P.A. Editor, Cambridge U. Press, U.K. 1993, pp. 48-93.
Ganguly, Karunesh et al.; Enhancement of presynaptic neuronal excitability by correlated presynaptic and postsynaptic spiking; *Nature Neuroscience*; vol. 3 No. 10, Oct. 2000, pp. 1018-1026.
Gary, Mary G., et al., *Evaluation of the Efficacy of a Bioerodible Bupivacaine Polymer System on Antinociception and Inflammatory Mediator Release*, Pain 82, 1999, pp. 49-55.
Gaspar, Laurie E., et al., *Permanent$^{125}$ Iodine Implants for Recurrent Malignant Gliomas*, Int. J. Radiation Oncology Biol. Phys. vol. 43, No. 5, 1999, pp. 977-982.
George et al., Ann. Otol. Rhino!. Laryngol. 101, 1992, pp. 888-892, abstract.
Ghika, J., et al., *Bilateral contemporaneous posteroventral pallidotomy for the treatment of Parkinson's disease: neuropsychological and neurological and neurological side effects, Report of four cases and review of the literature*, J. Neurosurg, Aug. 91(2), 1999, pp. 313-321.
Giladi N., J. Neurol. Sci. 152, 1997, pp. 132-135, abstract.
Gilio, F., M.D., et al., *Effects of Botulinum Toxin Type A on Intracortical Inhibition in Patients with Dystonia*, Annals of Neurology, vol. 48, No. 1, Jul. 2000, pp. 20-26.
Granana et al., Seminars in Pediatric Neurology 6, Sep. 1999, pp. 221-224.
Greenberg et al., Neurology 54, 2000, pp. 142-147.
Gross, Jeffrey D., et al., *Pallidotomy for Parkinson's Disease*, Textbook of Stereostatic and Functional Neurosurgery, 1998, Chapter 121, pp. 1153-1160.
Gross, Robert E. et al., *Relationship of lesion location to clinical outcome following microelectrode-guided pallidotomy for Parkinson's disease*, Brain 122, 1999, pp. 405-416.
Gross, Robert E., et al., *The effects of pallidotomy on Parkinson's Disease: study design and assessment techniques*, Acta Neurochir Suppl 68, 1997, pp. 24-28.
Guyton, Arthur C. et al., Textbook of Medical Physiology 10th ed; W.B. Saunders Company; pp. 685-697.
Habermann, E., *Tetanus toxin and botulinum A neurotoxin inhibit and at higher concentrations enhance noradrenaline outflow from particulate brain cortex in batch*, Naunyn Schmiedebergs Arch Pharmacol 318, 1981, pp. 105-111.
Hagenah, R., et al., *Effects of Type A Botulinum Toxin on the Cholinergic Transmission at Spinal Renshaw Cells and on the Inhibitory Action at Ia Inhibitory Interneurons*, Naunyn-Schmiedeberg's Arch. Pharmacol. 299, 1977, pp. 267-272.
Heikkinen, E.R. et al.; Stereotactic Radiotherapy Instead of Conventional Epilepsy Surgery; *Acta Neurochirurgica*; 1992, 1994, pp. 159-160.
Herrera, D.G., et al., Neuroscience 35(2), 1990pp. 273-281.
Hoffmann, Ralph E., et al., *Transcranial Magnetic Stimulation and Auditory Hallucinations in Schizophrenia*, The Lancet, vol. 355, Mar. 25, 2000, pp. 1073-1075.
Hutchison, W.D. et al., *Differential neuronal activity in segments of globus pallidus in Parkinson's disease patients*, NeuroReport, vol. 5, No. 12, Jul. 21, 1994, pp. 1533-1537.
Hutchison, W.D. et al., *Effects of apomorphine on globus pallidus neurons in Parkinsonian patients*, Annals of Neurology, No. 42, No. 5, 1997, pp. 767-775.
Hutchison, W.D., et al,. *Identification and characterization of neurons with tremor-frequency activity in human globus pallidus*, Exp Brain Res 113, 1997, pp. 557-563.
Huttner, W.B. et al.; Exocytotic and endocytotic membrane traffic in neurons; *Current Opinion in Neurobiology*; 1991, 1, pp. 388-392.

(56) References Cited

OTHER PUBLICATIONS

Jackowski, Andre, *Neural injury repair: hope for the future as barriers to effective CNS regeneration become clearer*, British Journal of Neurosurgery 9, 1995, pp. 303-317.
Jankovic J., In: Therapy with Botulinum Toxin (Ed) Jankovic J., Chapter 39, 1994, pp. 503-509.
Jankovic, Joseph; *Botulinum Toxin in the Treatment of Dystonic Tics*; Movment Disorders; vol. 9, No. 3, 1994; pp. 347-349.
Jankovic, Joseph; *Botulinum Toxin in the Treatment of Tics Associated with Tourette's Syndrome*; Neurology; Apr. 1993; 43(4 Suppl 2); A310; Abstract.
Jefferys, J.G.R. et al., Chronic focal epilepsy induced by intracerebral tetanus toxin; *The Italian Journal of Neurological Sciences*; 16, 1995, pp. 27-32.
Jellinger, K.A.; Post mortem studies in Parkinson's disease—is it possible to detect brain areas for specific symptoms?; *J Neural Transm.* 1999, Suppl 56, pp. 1-29.
Jimenez-Jimenez, F.J., et al., *Pharmacological Options for the Treatment of Tourette's Disorder*, Drugs, 2001, 61(15), pp. 2207-2220.
Jitpimolmard et al., J. Neruol Neurosurg Psychiatry 64, 1998, pp. 751-757.
Kaplitt, Michael G., MD., et al., *Surgical Drug Delivery for Neurodegenerative Diseases*, Clinical Neurosurgery, 2000, vol. 48, Chapter 10, pp. 127-144.
King, David B., *Parkinson's disease levodopa complications*, The Canadian Journal of Neurological Sciences 26, 1999, Suppl 2, pp. S13-S20.
Kohl, A. et al.; Comparison of the effect of botulinum toxin A (Botox®) with the highly-purified neurotoxin (NT 201) in the extensor digitorum brevis muscle test; *Movement Disorders*; 2000, 15, Suppl 3, 165, pp. 805.
Koller, W.C. et al.; Surgical treatment of Parkinson's disease; *Journal of the Neurological Sciences*; 167, 1999, pp. 1-10.
Korolkiewicz, Pharmacological Research 37, 1998, pp. 477-483.
Kossoff, E.H., et al. *Tourette Syndrome: Clinical Characteristics and Current Management Strategies*, Paediatr Drugs 3(5), 2001, pp. 355-363.
Krack, P., et al., *Modification of a Facial Tick with Botulinum Toxin*, Mov Disord 1995, May, 10(3), p. 401.
Krauss, Joachim K. et al., Severe Motor Tics Causing Cervical Myelopathy in Tourette's Syndrome; *Movement Disorders*; vol. 11, No. 5, 1996; pp. 563-565.
Kudelko, K.M. et al., *Successful treatment of recalcitrant restless legs syndrome with botulinum toxin A*; Movment Disorders; 2002; 17 (Suppl 5); S242 ABS p. 779.
Kwak et al., Arch. Neurol. 57, 2000, pp. 1190-1193.
Kwak, C., et al., *Premonitory Sensor Phenomenon in Tourette's Syndrome*, Mov. Disord. Dec. 2003, 18(12), pp. 1530-1533.
Kwak, Carolyn, et al., *Tics in Tourette Syndrome and Botulinum Toxin*, Journal of Child Neurology, vol. 15, No. 9, Sep. 2000.
Kwan, P. et al.; Refractory epilepsy: a progressive, intractable but preventable condition?; *Seizure*; 2000, 11, pp. 77-84.
Lan, J. et al., Activation of Metabotropic Glutamate Receptor 1 Accelerates NMDA Receptor Trafficking; *The Journal of Neuroscience*; Aug. 15, 2001, 21, (16), pp. 6058-6068.
Landi, A. et al.; Accuracy of Stereotactic Localisation with Magnetic Resonance Compared to CT Scan: Experimental Findings; *Acta Neurochir*, 2001, 143, pp. 593-601.
Lang et al., Adv. Neurol. 58, 1992, pp. 25-32.
Lang et al., Ann. Neurol. 33, 1993, pp. 212-215.
Lang, A., Neurology 41, 1991, pp. 223-228.
Lang, A.E., *Update on the Treatment of Tics*, Adv. Neurol. 85, 2001, pp. 355-362.
Lavenstein, B.L., *Treatment Approaches for Children with Tourette Syndrome*, Curr Neurol Neurosci Rep, Mar. 2003, 3(2), pp. 143-148.
Leckman et al., Am. J. Psychiatry 150, 1993, pp. 98-102.
Leckman et al., Am. J. Psychiatry 151, 1994, pp. 675-680.
Lee et al., J. Clin. Psychol. 32, 1976, pp. 843-844, abstract.

Levy, Ron et al.; Lidocaine and muscimol microinjections in subthalamic nucleus reverse parkinsonian symptoms; *Brain*. 2001, 124, pp. 2105-2118.
Lomber, Stephen G.; The advantages and limitations of permanent or reversible deactivation techniques in the assessment of nueral function; *Journal of Neuroscience Methods*; 86, 1999, pp. 109-117.
Lozano, Andres et al.; Methods for microelectrode-guided posteroventral pallidotomy; *J Neurosurg*; vol. 84, Feb. 1996, pp. 194-202.
Malpeli, Joseph; Reversible inactivation of subcortical sites by drug injection; *Journal of Neuroscience Methods*; 86, 1999, pp. 119-128.
Marjama-Lyons, Jill et al., *Tremor-Predominant Parkinson's Disease*; Drugs & Aging; 2000; Apr. 16 (4) pp. 273-278.
Marras et al., Neurology 56, Mar. 2001, pp. 605-610.
Martin, J.H. et al.; Pharmacological inactivation in the analysis of the central control of movement; *Journal of Neuroscience Methods*; 86, 1999, pp. 145-159.
Matarasso, S.L., Dermatol. Surg. 29, 2003, pp. 7-13, abstract.
McCormick, David et al.; On The Cellular and Network Bases of Epileptic Seizures; *Annual Rev Physiol*; 2001, 63, pp. 815-846.
Mellanby, Jane; Tetanus Toxin as a Tool for Investigating the Consequences of Excessive Neuronal Excitation; *Botulinum and Tetanus Neurotoxins*; edited by B.R. DasGupta, Plenum Press, 1993, pp. 291-297.
Merck Manual of Diagnosis and Therapy, 2002, Rahway, N.J., pp. 378, 1436, 1491-1495, 1500.
Merck Manual, Second Home Edition, Chapter 85, online version accessed Aug. 10, 2005.
Morrell, Frank et al.; Multiple subpial transaction: a new approach to the surgical treatment of focal epilepsy; *J Neurosurg*; 70, 1989, pp. 231-239.
Mulligan, Lisa et al.; Multiple Subpial Transections: The Yale Experience; *Epilepsia*; 42(2), 2001, pp. 226-229.
Nadeau, Stephen E.; Parkinson's Disease; *J by the American Geriatrics Society*, 1997, 45, pp. 233-240.
Naver et al., Eur. J. Neurol. Jan. 7, 2000, pp. 55-62.
Nowinski, Wieslaw et al.; Computer-Aided Stereotactic Functional Neurosurgery Enhanced by the Use of the Multiple Brain Atlas Database. *IEEE Transactions on Medical Imaging*;VI 19, No. 1, Jan. 2000, pp. 62-69.
Oakman, S.A. et al.; Characterization of the Extent of Pontomesencephalic Cholinergic Neurons' Projections to the Thalamus: Comparison with Projections to Midbrain Dopaminergic Groups; *Neuroscience*, vol. 94, No. 2, 1999, pp. 529-547.
Owe-Larsson, Bjorn et al.; Distinct Effects of Clostridial Toxins on Activity-dependent Modulation of Autaptic Responses in Cultured Hippocampal Neurons. *European Journal of Neuroscience*, vol. 9, 1997, pp. 1773-1777.
Parrent Andrew G. et al.; Stereotactic Surgery for Temporal Lobe Epilepsy. *The Canadian Journal of Neurological Sciences*, Suppl 1, pp. S79-S96.
Parrent, Andrew G.; Stereotactic radiofrequency ablation for the treatment of gelastic seizures associated with hypothalamic hamartoma; *J Neurosurg*, 91, 1999, pp. 881-884.
Parton, R.G. et al.; Cell Biology of Neuronal Endocytosis; *Journal of Neuroscience Research*, 1993, 36, pp. 1-9.
Pauls et al., Arch. Gen. Psychiatry 43, 1986, pp. 1180-1182.
Penn, Richard D.; The Future of CNS Infusion Systems; *Textbook of Stereotactic and Functional Neurosurgery*; edited by Gildenberg et al., McGraw-Hill publishers, Chp 218, pp. 2073-2076.
Perry, Elaine et al.; Acetylcholine in mind: a neurotransmitter correlate of consciousness?; *TINS*, 1999, vol. 22, No. 6, pp. 273-280.
Physician's Desk Reference, electronic version, entry for botulinum toxin BOTOX accessed Feb. 25, 2005.
Playfer, J.R.; Parkinson's disease; *Postgrad Med J*; 1997, 73, pp. 257-264.
Poungvarin et al., J. Med. Assoc. 78, Thailand, 1995, pp. 281-288.
Prince, David A.; Cellular Mechanisms of Interictal-ictal Transitions; *Mechanisms of Epileptogenesis The Transition to Seizure*; edited by Dichter, published by Plenum Press, Chp 4, pp. 57-71.

(56) References Cited

OTHER PUBLICATIONS

Prince, David A.; Epileptogenic Neurons and Circuits: *Jasper's Basic Mechanisms of the Epilepsies Third Edition: Advances in Neurology*; vol. 79, edited by Delgado-Escueta et al., 1999, Chp 45, pp. 665-684.
Rabasseda, Toxicon 26, 1998, pp. 329-336.
Racine, Ronald J.; Modification of Seizure Activity by Electrical Stimulation: I. After-Discharge Threshold; *Electroenceph din Neurophysiol*; 1972, 32, pp. 269-279.
Racine, Ronald J.; Modification of Seizure Activity by Electrical Stimulation: II. Motor Seizure; *Electroenceph clin Neurophysiol*; 1972, 32, pp. 281-294.
Raggenbass, Mario et al.; Nicotinic Receptors in Circuit Excitability and Epilepsy; *J Neurobiol*; Dec. 2002, 53(4) pp. 580-589.
Rand, Robert W. et al.; Intratumoral Administration of Recombinant Circularly Permuted interleukin-4-Pseudomonas Exotoxin in Patients with High-Grade Glioma; *Clinical Cancer Research*; 6(6), 2157, pp. 1-16 Abstract.
*Report of the Therapeutics and Technology Assessment Subcommittee of the American Academy of Neurology*, Neurology 40, 1990, pp. 1332-1336.
Rico, Beatriz et al.; A population of cholinergic neurons is present in the macaque monkey thalamus; *European Journal of Neuroscience*; vol. 10, 1998, pp. 2346-2352.
Robertson, J. Child Psycho!. Psychiatr. 35, 1994, pp. 597-611.
Rodriguez-Nunez, Antonio, *Syncope and Seizures: It Is Time for Evidence*, Journal of Child Neurology, vol. 15, No. 9, Sep. 2000.
Rogawski, Michael et al.; Antiepileptic Drugs: Pharmacological Mechanisms and Clinical Efficacy with Consideration of Promising Developmental Stage Compounds; *Pharmacological Reviews*; vol. 42, No. 3, pp. 223-286.
Salloway, Stephen, et al., *Botulinum Toxin for Refractory Vocal Tics*, Mov Disord 1996, 11(6), pp. 745-748.
Schafer, M.K. et al.; Cholinergic Neurons and Terminal Fields Revealed by Immunohistochemistry for the Vesicular Acetycholine Transporter. I. Central Nervous System; *Neuroscience*; vol. 84, No. 2, 1998, pp. 331-359.
Schantz, Edward J. et al., *Preparation and Characterization of Botulinum Toxin Type A for Human Treatment*; Terapy with Botulinum Toxin, edited by Jankovic et al., published by Marcel Dekker, Inc., Chpt. 3, pp. 41-49.
Schapiro, Pediatr. Nursing 28, May-Jun. 2002, pp. 243-253.
Scharfen, Cindy et al.; High *Activity Iodine-125 Interstitial Implant for Gliomas*; Int J Radiation Oncology Biol Phys; vol. 24, pp. 583-591.
Schuurman, P. R. et al.; A Comparison of Continuous Thalamic Stimulation and Thalamotomy for Suppression of Severe Tremor; *The New England Journal of Medicine*; Feb. 17, 2000, vol. 342, No. 7, pp. 461-468.
Scott, B.L., et al., *Botulinum toxin injection into vocal cord in the treatment of malignant coprolalia associated with Tourette's Syndrome*, Move. Disord., Jul. 1996 11(4), pp. 431-433.
Scremin et al., Brain Research Bulletin 45, 1998, pp. 167-174.
Silberstein, Stephen, et al,. *Botulinum Toxin Type A as a Migraine Preventive Treatment*, Headache, Jun. 2000 40(6), pp. 445-450.
Singer, H.S., et al,. *New Treatments for Tourette's Syndrome*, Inpharma 21, Spring 2001, No. 1284.
Smith, Epilepsia 34, 1993, pp. 43-53.
Speelman, J.D. et al.; Thalamic Surgery and Tremor; *Movement Disorders*; vol. 13, Suppl 3, 1998, pp. 103-106.
Stein et al., J. Clin. Psychiatr. 58, Apr. 1997, pp. 177-178.
Koliatsos et al., Eds. Steriade, M. et al., *Brain Cholinergic Systems*; Oxford University Press, 1990, pp. 136.

Steriade, M. et al.; Parallel activation of thalamic and cortical neurons by brainstem and basal forebrain cholinergic systems; *Brain Cholinergic Systems*; Oxford University Press, 1990, Chp 1, pp. 4-64.
Stone, Trevor W., editor, *CNS Neurotransmitters and Neuromodulators Acetylcholine*; CRC Press, 1995, pp. 16.
Sugahara, H. et al., *Psychogenic Torticollis*, Ryoikibetsu Khokogun Shirizu 38 (article in Japanese), 2003, pp. 582-586, Abstract.
Sun, Bomin et al.; Reduction of Hippocampal-Kindled Seizure Activity in Rats by Stereotactic Radiosurgery; *Experimental Neurology*; 154, 1998, pp. 691-695.
Sutula, Thomas P.; Sprouting as an underlying cause of hyperexcitability in experimental models and in the human epileptic temporal lobe; *Epilepsy: Models, Mechanisms, and Concepts*; edited by Schwartzkroin, Cambridge Univ Press, Chp 9, pp. 304-322.
Talairach, Jean et al.; editors, *Co-Planar Stereotaxic Atlas of the Human Brain*; Chapter 1: Direct and Indirect Radiologic Localization pp. 1-4 and Chapter 2: Reference System: Basal Brain Line CA-CP pp. 5-8, 1988, Thieme Medical Publishers, Inc., N.Y.
Tarsy, D.; Botulinum Toxin Treatment is not Effective for Epilepsy Partialis Continua; *Movement Disorders*; 1995, 10(3) pp. 357-358.
Tasker, Ronald R. et al.; Surgical Treatment of the Dystonias; *Textbook of Stereotactic and Functional Neurosurgery*; edited by Gildenberg et al.; Chp 105, pp. 1015-1032.
Cullen et al., Eds. Tracey, David J. et al., *Neurotransmitters in the Human Brain*; Plenum Press, 1995, pp. 136-139.
Trimble, Michael R., et al., *Vocal Tics in Gilles de la Tourette Syndrome Treated with Botulinum Toxin Injection*, Mov Disord., May 1998, 13(3), pp. 617-619.
Trudeau, Louis-Eric et al.; Modulation of an early step in the secretory machinery in hippocampal nerve terminals; *Neurobioloy*; vol. 95, Issue 12, Jun. 9, 1998, pp. 7163-7168, Abstract.
Tyas, Suzanne et al., Risk Factors for Alzheimer's Disease: A Population-Based, Longitudinal Study in Manitoba, Canada, International Journal of Epidemiology, 2001, 590-597, 30.
Wang, Lu-Yang et al.; High-frequency firing helps replenish the readily releasable pool of synaptic vesicles; *Nature*; vol. 394, Jul. 23, 1998, pp. 384-388.
Weinlander et al., J. Clin. Psychol. 34, 1978, pp. 31-32.
Weinlander et al., J. Psychol. 92, 1976, pp. 77-78, abstract.
Wiebe, Samuel et al.; A Randomized, controlled Trial of Surgery for Temporal-Lobe Epilepsy; The New England Journal of Medicine; vol. 345, No. 5, Aug. 2, 2001, pp. 311-318.
Wohlfarth et al., Naunyn Schmideberg's Arch. Pharmacolo. 335, 1997, pp. 335-340.
Zigmond, et al., *Fundamental Neuroscience*; 1999 by Academic Press, San Diego, CA; pp. 963-964.
Lang, Amy M., Botulinum Toxin Type A Therapy in Chronic Pain Disorders, Archives of Physical Medicine and Rehabilitation, Mar. 2003, S69-S73, 84 (Suppl 1), US.
Aoki, Roger Kei et al, Mechanisms of the Antinociceptive Effect of Subcutaneous Botox Inhibition of Peripheral and Central Nociceptive Processing, Cephalalgia, 2003, 649 (1 Page), 23.
Gary E. Bordic, et al., The Use of Botulinum Toxin for the Treatment of Chronic Facial Pain, The Journal of Pain, Feb. 20002, 22-27, 3 (1), US.
Aoki, K. Roger, Evidence for Antinociceptive Activity of Botulinum Toxin Type A in Pain Management, Headache 2003, Aug. 2003, S9-S15, 43 (Supp 1), US.
Kurata, Kouichi, et al., Complete Remission of Neuroleptic-Induced Meige's Syndrome by Botulinum Toxin Treatment: A Case Report, The Japanese Journal of Psychiatry and Neurology, 1993, 115-119, 47, US.
Laskawi, R., et al., Essential blepharospasm and botulinum toxin an electrophysiologic study, HNO, Jan. 1990, 29-32, 38, DE.
Auger, Raymond G., Hemimasticatory Spasm: Clinical and Electrophysiologic Observations, Neurology 1992, Dec. 1992, 2263-2266, 42, US.

\* cited by examiner

BOTULINUM TOXIN TREATMENTS OF NEUROLOGICAL AND NEUROPSYCHIATRIC DISORDERS

CROSS REFERENCE

This application is a continuation of U.S. application Ser. No. 14/247,469, filed Apr. 8, 2014, which is a continuation of U.S. application Ser. No. 10/964,898, filed Oct. 12, 2004, now U.S. Pat. No. 8,734,810, which claims the benefit of provisional application No. 60/574,957, filed May 26, 2004, provisional application No. 60/556,150, filed Mar. 24, 2004 and provisional application No. 60/515,362, filed Oct. 29, 2003, respectively, the entire contents of which applications are incorporated herein by reference in their entireties.

BACKGROUND

The present invention is directed to medicaments and methods for treating (including alleviating and/or preventing) neuropsychiatric and/or neurological disorders, including chronic neurological disorders, such as neurological disorders mediated by or influenced by the thalamus. In particular, the present invention is directed to a medicament containing a botulinum toxin for treating a neuropsychiatric and/or a chronic neurological disorder by administering the botulinum toxin to a trigeminal nerve.

A neurological disorder is a central nervous system malfunction. The central nervous system includes the brain. The brain includes the dorsal end of the spinal cord, medulla, brain stem, pons, cerebellum, cerebrum and cortex.

Epilepsy

Epilepsy describes a condition in which a person has recurrent seizures due to a chronic, underlying process. A seizure is a paroxysmal event due to abnormal, excessive, hypersynchronous discharges from an aggregate of central nervous system neurons. Among the many causes of epilepsy, there are various epilepsy syndromes in which the clinical and pathologic characteristics are distinctive and suggest a specific underlying etiology. The prevalence of epilepsy has been estimated at 5 to 10 people per 1000 population. Severe, penetrating head trauma is associated with up to a 50% risk of leading to epilepsy. Other causes of epilepsy include stroke, infection and genetic susceptibility.

Antiepileptic drug therapy is the mainstay of treatment for most patients with epilepsy and a variety of drugs have been used. See e.g., Fauci, A. S. et al., *Harrison's Principles of Internal Medicine*, McGraw-Hill, 14$^{th}$ Edition (1998), page 2321. Twenty percent of patients with epilepsy are resistant to drug therapy despite efforts to find an effective combination of antiepileptic drugs. Surgery can then be an option. Video-EEC monitoring can be used to define the anatomic location of the seizure focus and to correlate the abnormal electrophysiologic activity with behavioral manifestations of the seizure. Routine scalp or scalp-sphenoidal recordings are usually sufficient for localization. A high resolution MRI scan is routinely used to identify structural lesions. Functional Imaging studies such as SPECT and PET are adjunctive tests that can help verify the localization of an apparent epileptogenic region with an anatomic abnormality.

Once the presumed location of the seizure onset is identified, additional studies, including neuropsychological testing and the intracarotid amobarbital test (Wada's test) can be used to assess language and memory localization and to determine the possible functional consequences of surgical removal of the epileptogenic region. In some cases, the exact extent of the resection to be undertaken can be determined by performing cortical mapping at the time of the surgical procedure. This involves electrophysiologic recordings and cortical stimulation of the awake patient to identify the extent of epileptiform disturbances and the function of the cortical regions in questions.

The most common surgical procedure for patients with temporal lobe epilepsy involves resection of the anteromedial temporal lobe (temporal lobotomy) or a more limited removal of the underlying hippocampus and amygdala. Focal seizures arising from extratemporal regions may be suppressed by a focal neocortical resection. Unfortunately, about 5% of patients can still develop clinically significant complications from surgery and about 30% of patients treated with temporal lobectomy will still have seizures.

Focal epilepsy can involve almost any part of the brain and usually results from a localized lesion of functional abnormality. One type of focal epilepsy is the psychomotor seizure. Current therapy includes use of an EEG to localize abnormal spiking waves originating in areas of organic brain disease that predispose to focal epileptic attacks, followed by surgical excision of the focus to prevent future attacks.

Chronic Pain

About one third of a population will experience chronic pain. In the United States chronic pain is the most common cause of long-term disability, partially or totally disabling about fifty million people. As the population ages, the number of people needing treatment for chronic pain from back disorders, degenerative joint diseases, rheumatologic conditions, fibromyalgia, visceral diseases, and cancers can be expected to increase.

Various events such as tissue injury can trigger pain signals to the brain. These electrical impulses are carried by thin unmyelinated nerves called nociceptors (C-fibers) that synapse with neurons in the dorsal horn of the spinal cord. From the dorsal horn, the pain signal is transmitted via the spinothalamic tract to the cerebral cortex, where it is perceived, localized and interpreted.

Chronic pain is not just a prolonged version of acute pain. As pain signals are repeatedly generated, neural pathways undergo physiochemical changes that make the central nervous system hypersensitive to the pain signals and resistant to antinociceptive input. This is called central sensitization.

Fibromyalgia is a chronic pain syndrome believed due to central sensitization. Characteristic symptoms of fibromyalgia include widespread pain, fatigue, sleep abnormalities and distress. Patients with fibromyalgia show psychophysical evidence of hyperalgesia, that is a heightened response to mechanical, thermal and electrical stimuli at various tender or trigger points. In fibromyalgia the sensation at these tender points is much more pronounced and patients have a decreased threshold of pain, responding to even minimal amounts of pressure. The Copenhagen Fibromyalgia Symposium defined fibromyalgia as a situation in which a patient has at least 11 of 18 specified tender points, present in all four quadrants of the body. Primary hyperalgesia develops in an area where injury to tissues has occurred and secondary hyperalgesia may be found in undamaged tissue. Peripheral and central abnormalities of nociception have also been described in fibromyalgia. Important nociceptor systems in the skin and muscles seem to undergo profound changes in patients with fibromyalgia through unknown mechanisms. They include sensitization of vanilloid receptor, acid-sensing ion channel receptors and purino-receptors. Tissue mediators of inflammation and nerve growth factors can excite these receptors and cause extensive changes in pain sensitivity, but patients with fibromyalgia lack consistent evidence for inflammatory soft tissue abnormalities.

Therefore, recent investigations have focused on central nervous system mechanisms of pain in fibromyalgia. Treatments for fibromyalgia include steroid trigger point injections and medications such as tricyclic antidepressants, neurontin, and narcotics, but these all have negative side effects.

Post Stroke Pain

Pain can be debilitating and it is not uncommon to attribute widespread pain in the elderly to osteoarthritis within the spinal column structures and peripheral joints or to other musculoskeletal conditions. However, if pain is widespread and exhibits neuropathic features, such as dysaesthesias (poorly localized burning sensations that occur after a stimulus is applied), allodynia (triggered by stimuli which are not normally painful or pain which occurs other than in the area stimulated), hyperpathia (increased pain from normally painful stimuli) and hyperalgesia, it can be the result of a lesion or disorder such as Thalamic Pain Syndrome or Central Post-Stroke Pain (CPSP) originating from the central nervous system. The source of the pain is via the thalamus, the sensory processing center within the central nervous system.

A stroke is the result of loss of the blood supply to a part of the brain and can result in weakness and slurred speech. CPSP develops in about 8% of stroke patients, occurring within one to six months after the stroke. Common painkillers often have no effect on this pain, although some medications developed for epilepsy and depression may reduce pain after strokes. CPSP has also been treated with intravenous lidocaine or oral opioids, as well as amitriptyline, carbamazepine, tegretol and lamotrigine, but these medications have adverse side effects.

Regional Pain Syndrome

Complex Regional Pain Syndrome (CRPS) (also called Reflex Sympathetic Dystrophy Syndrome) is a chronic condition characterized by severe burning pain, pathological changes in bone and skin, excessive sweating, tissue swelling, and extreme sensitivity to touch. The syndrome is a nerve disorder that occurs at the site of an injury (most often to the arms or legs), and the disorder is unique in that it simultaneously affects the nerves, skin, muscles, blood vessels, and bones. It occurs especially after injuries from high-velocity impacts such as those from bullets or shrapnel. However, it may occur without apparent injury. CRPS is believed to be the result of dysfunction in the central or peripheral nervous systems. CRPS I is frequently triggered by tissue injury; the term describes all patients with the above symptoms but with no underlying nerve injury. Patients with CRPS II experience the same symptoms but their cases are dearly associated with a nerve injury. CRPS can strike at any age but is more common between the ages of 40 and 60, although the number of CRPS cases among adolescents and young adults is increasing. CRPS affects both men and women, although most experts agree that it is more common in young women. One visible sign of CRPS near the site of injury is warm, shiny red skin that later becomes cool and bluish.

The pain that patients report is out of proportion to the severity of the injury and gets worse, rather than better, over time. Eventually the joints become stiff from disuse, and the skin, muscles, and bone atrophy. The symptoms of CRPS vary in severity and duration, and early treatment often results in remission. If treatment is delayed, however, the disorder can quickly spread to the entire limb, and changes in bone and muscle may become irreversible. In 50 percent of CRPS cases, pain persists longer than 6 months and sometimes for years. Physicians use a variety of drugs to treat CRPS. Elevation of the extremity and physical therapy are also used to treat CRPS. Injection of a local anesthetic is usually the first step in treatment. TENS (transcutaneous electrical stimulation), a procedure in which brief pulses of electricity are applied to nerve endings under the skin, has helped some patients in relieving chronic pain. In some cases, surgical or chemical sympathectomy (interruption of the affected nerve(s) of the sympathetic nervous system) is performed to relieve pain, but these treatments may also destroy other sensations as well.

Phantom Limb Pain

Phantom limb pain is a conscious feeling of a painful limb, after the limb has been amputated. The brain creates a "whole body map" which remains intact even when a piece of the body no longer exists and phantom sensation or pain can result *when the brain sends persistent messages to limbs not there. Phantom pain or sensations can range in type and intensity. For example, a mild form might be experienced as a sharp, intermittent stabbing pain causing the limb to jerk in reaction to the pain. An example of a more severe type might be the feeling that the missing limb is being crushed. Usually phantom limb pain diminishes in frequency and intensity over time. For a small number of amputees, however, phantom limb pain can become chronic and debilitating because of the frequency and severity of the pain. Anesthetics such as lidocaine, marcaine, novocaine, pontocaine, and xylocaine are often used to prevent nerve cells from transmitting pain messages, thus relieving trigger points and reducing stump pain, but their effects are temporary. Anti-inflammatories (acetaminophen, aspirin, ibuprofen), antidepressants (Amitriptyline, Elavil, Pamelor, Paxil, Prozac, Zoloft), anticonvulsants (Tegretol, Neurontin) and narcotics (Codeine, Demerol, Morphine, Percodan, Percocet) are other medications also used to treat phantom pain, but these often have adverse side effects.

Demyelinating Disease Pain

Demyelinating diseases such as Multiple Sclerosis (MS), progressive multifocal leukoencephalopathy (PML), disseminated necrotizing leukoencephalopathy (DNL), acute disseminated encephalomyelitis, and Schilder disease are acquired chronic, inflammatory diseases that result in the destruction of myelin, the fatty insulation normally covering the nerve fibers that aids in the transmission of nerve impulses. Demyelination results in impaired transmission of action potentials along exposed axons, producing a multiplicity of neurological deficits, for example, sensory loss, weakness, visual loss, vertigo, incoordination, sphincter disturbances, and altered cognition. MS is usually characterized by a relapsing-remitting course in the early stages, with full or nearly full recovery, initially. Over time the disease enters an irreversible progressive phase of neurological deficit. Acute relapses are caused by inflammatory demyelination, while disease progression is thought to result from axonal loss. The disease process affects myelinated fibre tracts, such as the optic nerves and the white matter tracts of the brain and spinal cord. This may lead to a variety of symptoms, such as visual disturbances, bladder, bowel or sexual dysfunction, motor weakness and spasticity, sensory symptoms (numbness, dysaesthesia), cerebellar symptoms (tremor and ataxia), and other symptoms (fatigue, cognitive impairment and psychiatric complications). Therapies used to treat demyelinating disorders can be categorized into disease modifying therapies, drugs used in acute exacerbations and drugs used to treat disease complications. So far, no disease modifying therapy has been found that halts disease progression or improves neurological status.

For this reason, the mainstay of treatment remains symptomatic management. Current therapies predominantly influence the immune system and target the inflammatory processes that are involved in the disease pathology. Beta interferons (interferon beta-1b, known as Betaferon), glatiramer acetate (Copaxone) and mitoxantrone have been used for their immunomodulatory effects. These include inhibition of leukocyte proliferation and antigen presentation, inhibition of T-cell migration across the blood-brain barrier and modulation of cytokine production to produce an anti-inflammatory environment. Oral steroids, such as prednisolone, may be effective in shortening acute attacks of MS. Other potential therapies are undergoing clinical evaluation, including T-cell vaccination, interleukin 10, matrix metalloproteinase inhibitors, plasmapheresis, vitamin D, retinoic acid, ganciclovir, valaciclovir, bone marrow transplantation and autologous stem cell transplantation.

As indicated, various therapeutic treatments are available to as treatments for various neurological disorders, such as thalamically mediated disorders. However, these therapeutic treatments have several adverse side-effects. These side-effects may be attributed to the fact that the pharmaceutical agents are typically administered systemically, and therefore, the agents have a relatively non-specific action with respect to the various biological systems of the patient. For example, administration of benzodiazepines may result in sedation and muscle relaxation. In addition, tolerance may develop to these drugs, as well as withdrawal seizures may develop. Current therapeutic strategies also require consistent and repeated administration of the agents to achieve the desired effects.

Neuropsychiatric Disorders

A neuropsychiatric disorder is a neurological disturbance that is typically labeled according to which of the four mental faculties is affected. For example, one group of neuropsychiatric disorders includes disorders of thinking and cognition, such as schizophrenia and delirium. A second group of neuropsychiatric disorders includes disorders of mood, such as affective disorders and anxiety. A third group of neuropsychiatric disorders includes disorders of social behavior, such as character defects and personality disorders. And a fourth group of neuropsychiatric disorders includes disorders of learning, memory, and intelligence, such as mental retardation and dementia. Accordingly, neuropsychiatric disorders encompass schizophrenia, delirium, Alzheimer's disease, depression, mania, attention deficit disorders, drug addiction, dementia, agitation, apathy, anxiety, psychoses, personality disorders, bipolar disorders, obsessive-compulsive disorders, eating disorders, post-traumatic stress disorders, irritability, and disinhibition.

Schizophrenia

Schizophrenia is a disorder that affects about one percent of the world population. Three general symptoms of schizophrenia are often referred to as positive symptoms, negative symptoms, and disorganized symptoms. Positive symptoms can include delusions (abnormal beliefs), hallucinations (abnormal perceptions), and disorganized thinking. The hallucinations of schizophrenia can be auditory, visual, olfactory, or tactile. Disorganized thinking can manifest itself in schizophrenic patients by disjointed speech and the inability to maintain logical thought processes. Negative symptoms can represent the absence of normal behavior. Negative symptoms include emotional flatness or lack of expression and can be characterized by social withdrawal, reduced energy, reduced motivation, and reduced activity. Catatonia can also be associated with negative symptoms of schizophrenia. The symptoms of schizophrenia should continuously persist for a duration of about six months in order for the patient to be diagnosed as schizophrenic. Based on the types of symptoms a patient reveals, schizophrenia can be categorized into subtypes including catatonic schizophrenia, paranoid schizophrenia, and disorganized schizophrenia.

The brains of schizophrenic patients are often characterized by enlarged lateral ventricles, which can be associated with a reduction of the hippocampus and an enhancement in the size of the basal ganglia. Schizophrenic patients can also have enlarged third ventricles and widening of sulci. These anatomical characterizations point to a reduction in cortical tissue.

Although the cause of schizophrenia is not precisely known, there are several hypotheses. One hypothesis is that schizophrenia is associated with increased dopamine activity within the cortical and limbic areas of the brain. This hypothesis is supported by the therapeutic effects achieved by antipsychotic drugs that block certain dopamine receptors. In addition, amphetamine use can be associated with schizophrenia-like psychotic symptoms, and it is known that amphetamines act on dopamine receptors.

Examples of antipsychotic drugs that may be used to treat schizophrenic patients include phenothiazines, such as chlorpromazine and triflupromazine; thioxanthenes, such as chlorprothixene; fluphenazine; butyrophenones, such as haloperidol; loxapine; mesoridazine; molindone; quetiapine; thiothixene; trifluoperazine; perphenazine; thioridazine; risperidone; dibenzodiazepines, such as clozapine; and olanzapine. Although these agents may relieve the symptoms of schizophrenia, their administration can result in undesirable side effects including Parkinson's disease-like symptoms (tremor, muscle rigidity, loss of facial expression); dystonia; restlessness; tardive dyskinesia; weight gain; skin problems; dry mouth; constipation; blurred vision; drowsiness; slurred speech and agranulocytosis.

Antipsychotic drugs are believed to primarily act on dopamine receptors with a particular affinity for the $D_2$, $D_3$, and $D_4$ receptors. It is believed that the $D_3$ and $D_4$ receptors may have a higher affinity for certain antipsychotics, such as clozapine, as compared to the others. The brains of schizophrenic patients appear to have increased numbers of $D_2$ receptors in the caudate nucleus, the nucleus accumbens (ventral striatum), and the olfactory tubercle.

Dopamine neurons may be organized into four major subsystems: the tuberoinfundibular system; the nigrostriatal system; the mesolimbic system; and the mesocortical system. The tuberoinfundibular dopaminergic system originates in cell bodies of the arcuate nucleus of the hypothalamus and projects to the pituitary stalk. This system may be involved in secondary neuroendocrine abnormalities in schizophrenia. The nigrostriatal dopaminergic system originates in the substantia nigra and projects primarily to the putamen and the caudate nucleus. The mesolimbic dopaminergic system originates in the ventral tegmental area and projects to the mesial component of the limbic system, which includes the nucleus accumbens, the nuclei of the stria terminalis, parts of the amygdala and hippocampus, the lateral septal nuclei, and the mesial frontal, anterior cingulate, and entorhinal cortex. The nucleus accumbens is a convergence site from the amygdala, hippocampus, entorhinal area, anterior cingulate area, and parts of the temporal lobe. Thus, the mesolimbic dopaminergic projection can modulate and transform information conveyed from the nucleus accumbens to the septum, hypothalamus, anterior cingulate area, and frontal lobes, and overactive modulation of the nucleus accumbens output to these areas can contribute to positive symptoms associated with schizophrenia. The mesocortical dopaminergic system originates in the ventral tegmental area and projects to the neocortex and heavily to the prefrontal cortex. This component may be important in the negative symptoms of schizophrenia.

The ventral tegmental area, which is the source of origination of the dopaminergic input to the nucleus accumbens, receives a cholinergic input from the pedunculopontine nuclei of the brainstem. The pedunculopontine nucleus provides an excitatory cholinergic input to the ventral tegmental area (Clarke et al., *Innervation of substantia nigra neurons by cholinergic afferents from the pedunculopontine nucleus in the rat. Neuroanatomical and electrophysiological evidence*, Neuroscience, 23:1011-1019, 1987). It has been reported that schizophrenic patients have an increased number of cholinergic neurons in the pedunculopontine nuclei (Garcia-Rill et al., *Mesopontine neurons in schizophrenia*, Neuroscience, 66(2):321-335, 1995). However, these results were not confirmed in one study (German et al., *Mesopontine cholinergic and non-cholinergic neurons in schizophrenia*, Neuroscience, 94(1):33-38, 1999).

Mania

Mania is a sustained form of euphoria that affects millions of people in the United States who suffer from depression. Manic episodes can be characterized by an elevated, expansive, or irritable mood lasting several days, and is often accompanied by other symptoms, such as, overactivity, overtalkativeness, social intrusiveness, increased energy, pressure of ideas, grandiosity, distractibility, decreased need for sleep, and recklessness. Manic patients can also experience delusions and hallucinations.

Depressive disorders can involve serotonergic and noradrenergic neuronal systems based on current therapeutic regimes that target serotonin and noradrenalin receptors. Serotonergic pathways originate from the raphe nuclei of the brain stem, and noradrenergic pathways originate from the locus coeruleus. Decreasing the electrical activity of neurons in the locus coeruleus can be associated with the effects mediated by depression medications.

Mania may results from an imbalance in certain chemical messengers within the brain. It has been proposed that mania is attributed to a decline in acetylcholine. A decline in acetylcholine may result in a relatively greater level of norepinephrine. Administering phosphatidyl choline has been reported to alleviate the symptoms of mania.

Anxiety

Anxiety disorders may affect between approximately ten to thirty percent of the population, and can be characterized by frequent occurrence of symptoms of fear including arousal, restlessness, heightened responsiveness, sweating, racing heart, increased blood pressure, dry mouth, a desire to run or escape, and avoidance behavior. Generalized anxiety persists for several months, and is associated with motor tension (trembling, twitching, muscle aches, restlessness); autonomic hyperactivity (shortness of breath, palpitations, increased heart rate, sweating, cold hands), and vigilance and scanning (feeling on edge, exaggerated startle response, difficult in concentrating).

Benzodiazepines, which enhance the inhibitory effects of the gamma aminobutyric acid (GABA) type A receptor, are frequently used to treat anxiety. Buspirone is another effective anxiety treatment.

Alzheimer's Disease

Alzheimer's disease is a degenerative brain disorder characterized by cognitive and noncognitive neuropsychiatric symptoms, which accounts for approximately 60% of all cases of dementia for patients over 65 years old. Psychiatric symptoms are common in Alzheimer's disease, with psychosis (hallucinations and delusions) present in approximately fifty percent of affected patients. Similar to schizophrenia, positive psychotic symptoms are common in Alzheimer's disease. Delusions typically occur more frequently than hallucinations. Alzheimer's patients may also exhibit negative symptoms, such as disengagement, apathy, diminished emotional responsiveness, loss of volition, and decreased initiative.

Alzheimers disease patients may also exhibit enlargement of both lateral and third ventricles as well as atrophy of temporal structures.

It is possible that the psychotic symptoms of Alzheimer's disease involve a shift in the concentration of dopamine or acetylcholine, which may augment a dopaminergic/cholinergic balance, thereby resulting in psychotic behavior. For example, it has been proposed that an increased dopamine release may be responsible for the positive symptoms of schizophrenia. This may result in a positive disruption of the dopaminergic/cholinergic balance. In Alzheimer's disease, the reduction in cholinergic neurons effectively reduces acetylcholine release resulting in a negative disruption of the dopaminergic/cholinergic balance. Indeed, antipsychotic agents that are used to relieve psychosis of schizophrenia are also useful in alleviating psychosis in Alzheimer's patients.

Several of the symptoms associated with neuropsychiatric disorders appear to be, at least in part, attributed to hyperexcitability (i.e. sensitization to afferent input from peripheral nerves) of neurons within the brain. This interpretation is supported by the pharmacology associated with current therapeutic treatments. For example, many of the antipsychotic treatments are directed to interfering with binding of dopamine to dopamine receptors, as discussed above. Similarly, mania and anxiety are often treated with benzodiazepines, which enhance the inhibitory effects of GABA-mediated inhibition. U.S. Pat. No. 6,306,403 discloses intracranial administration of a botulinum toxin to treat various movement disorders. Additionally, it is known that stereotactic procedures can be used to administer a pharmaceutical to a discrete brain area to successfully alleviate a parkinsonian tremor. See e.g. Pahapill P. A., et al., *Tremor arrest with thalamic microinjections of muscimol in patients with essential tremor*, Ann Neur 46(2); 249-252 (1999).

However, current therapeutic treatments result in several adverse side-effects. These side-effects may be attributed to the fact that the pharmaceutical agents are typically administered systemically, and therefore, the agents have a relatively non-specific action with respect to the various biological systems of the patient. For example, administration of benzodiazepines may result in sedation and muscle relaxation. In addition, tolerance may develop to these drugs, as well as withdrawal seizures may develop. Current therapeutic strategies also require consistent and repeated administration of the agents to achieve the desired effects.

Trigeminal Nerve

The trigeminal nerve has three major branches, a number of smaller branches and is the great sensory nerve of the head and neck, carrying touch, temperature, pain, and proprioception (position sense) signals from the face and scalp to the brainstem. Trigeminal sensory fibers originate in the skin, course toward the trigeminal ganglion (a sensory nerve cell body), pass through the trigeminal ganglion, and travel within the trigeminal nerve to the sensory nucleus of the trigeminal nerve located in the brainstem.

The three major branches of the trigeminal nerve are the ophthalmic ($V_1$, sensory), maxillary ($V_2$, sensory) and mandibular ($V_3$, motor and sensory) branches. The large trigeminal sensory root and smaller trigeminal motor root leave the brainstem at the midlateral surface of pons. The sensory root terminates in the largest of the cranial nerve nuclei which extends from the pons all the way down into the second cervical level of the spinal cord. The sensory root joins the trigeminal or semilunar ganglion between the layers of the dura mater in a depression on the floor of the middle crania fossa. The trigeminal motor root originates from cells located in the masticator motor nucleus of trigeminal nerve located in the midpons of the brainstem. The motor root passes through the trigeminal ganglion and combines with the corresponding sensory root to become the mandibular nerve. It is distributed to the muscles of mastication, the mylohyoid muscle and the anterior belly of the digastric. The three sensory branches of the trigeminal nerve emanate from the ganglia to form the three branches of the trigeminal nerve. The ophthalmic and maxillary branches travel in the wall of the cavernous sinus just prior to leaving the cranium. The ophthalmic branch travels through the superior orbital fissure and passes through the orbit to reach the skin of the forehead and top of the head. The maxillary nerve enters the cranium through the foramen rotundum via the pterygopalatine fossa. Its sensory branches reach the pterygopalatine fossa via the inferior orbital fissure (face, cheek and upper teeth) and pterygopalatine canal (soft and hard palate, nasal cavity and pharynx). There are also meningeal sensory branches that enter the trigeminal ganglion within the cranium. The sensory part of the mandibular nerve is composed of branches that carry general sensory information from the mucous membranes of the mouth and cheek, anterior two-thirds of the tongue, lower teeth, skin of the lower jaw, side of the head and scalp and meninges of the anterior and middle cranial fossae.

The sensory nuclei of the trigeminal nerve are located within the brainstem, in the dorsolateral pons. The mesencephalic tract and the motor nucleus of the trigeminal nerve lie more medially. The superior cerebellar peduncle lies posteriorly. It is continuous inferiorly with the spinal nucleus of the trigeminal nerve that extends into the medulla. Superiorly, the sensory nuclei on each side are continuous with the mesencephalic nucleus.

Importantly, the sensory nuclei of the trigeminal nerve receive afferent (sensory input) fibres from: (1) the trigeminal nerve ophthalmic division (e.g. general sensation from supraorbital area, cornea, iris, ethmoid sinuses), (2) trigeminal nerve maxillary division (e.g. sensation from temple, cheek, oral cavity, upper pharynx), and (3) trigeminal nerve mandibular division (e.g. sensation from middle cranial fossa, inner cheek, anterior two thirds of the tongue, chin), (4) facial nerve (e.g. general sensation from external auditory meatus), (5) glossopharyngeal nerve (e.g. general sensation from middle ear, tonsils, oropharynx, posterior one third of the tongue), (6) vagus nerve (auricular, meningeal, internal laryngeal and recurrent laryngeal branches).

Thus, primary neurons in the trigeminal ganglion synapse on the main sensory trigeminal nucleus and on the spinal trigeminal nucleus in the brainstem. The spinal nucleus of the trigeminal system extends to the upper cervical spine, where connections with cervical dermatomes exist. These dermatomes are innervated by the cervical plexus, which has sensory branches from C1 to C4. The trigeminal nerve also innervates stretch receptors in the muscles of mastication. The cell bodies of these neurons are in the mesencephalic trigeminal nucleus in the midbrain and pons).

As indicated by FIG. 1, the ascending (afferent) second order trigeminal neurons from the main sensory trigeminal nucleus, and the ascending second order neurons from the spinal trigeminal nucleus ascend and synapse in the thalamus. Projections from the thalamus are to the facial representation of the sensory cortex. Central projections from the mesencephalic trigeminal nucleus are to the motor cortex. Thalamic projections to the sensory cortex follow a somatotopic organization. The hand and face have disproportionately greater representation on a homunculus map. This body map is not static, but dynamically controlled by the pattern of use, with increased use leading to increased cortical representation. Notably, the primary somatosensory cortex in the post central gyrus, receives input from the thalamus, and projects to the secondary somatic sensory cortex in the parietal operculum. There are also efferent connections from the sensory cortex to the motor cortex. Notably, the trigeminal nerve is a very large nerve and 28% of the sensory cortex is devoted to it alone.

Botulinum Toxin

The genus *Clostridium* has more than one hundred and twenty seven species, grouped according to their morphology and functions. The anaerobic, gram positive bacterium *Clostridium botulinum* produces a potent polypeptide neurotoxin, botulinum toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The botulinum toxin can apparently pass unattenuated through the lining of the gut and shows a high affinity for cholinergic motor neurons. Symptoms of botulinum toxin intoxication can progress from difficulty walking, swallowing and speaking to paralysis of the respiratory muscles and death.

Botulinum toxin type A is the most lethal natural biological agent known to man. About 50 picograms of a commercially available botulinum toxin type A (purified neurotoxin complex, Available from Allergan, Inc., of Irvine, Calif. under the tradename BOTOX® in 100 unit vials) is a LD50 in mice (i.e. 1 unit). One unit of BOTOX® contains about 50 picograms (about 56 attomoles) of botulinum toxin type A complex. Interestingly, on a molar basis, botulinum toxin type A is about 1.8 billion times more lethal than diphtheria, about 600 million times more lethal than sodium cyanide, about 30 million times more lethal than cobra toxin and about 12 million times more lethal than cholera. Singh, *Critical Aspects of Bacterial Protein Toxins*, pages 63-84 (chapter 4) of Natural Toxins II, edited by B. R. Singh et al., Plenum Press, New York (1976) (where the stated LD50 of botulinum toxin type A of 0.3 ng equals 1 U is corrected for the fact that about 0.05 ng of BOTOX® equals 1 unit). One unit (U) of botulinum toxin is defined as the LD50 upon intraperitoneal injection into female Swiss Webster mice weighing 18 to 20 grams each.

Seven generally immunologically distinct botulinum toxins have been characterized, these being respectively botulinum toxin serotypes A, B, $C_1$, D, E, F and G each of which is distinguished by neutralization with type-specific antibodies. The different serotypes of botulinum toxin vary in the animal species that they affect and in the severity and duration of the paralysis they evoke. For example, it has been determined that botulinum toxin type A is 500 times more potent, as measured 1*o* by the rate of paralysis produced in the rat, than is botulinum toxin type B. Additionally, botulinum toxin type B has been determined to be non-toxic in primates at a dose of 480 U/kg which is about 12 times the primate LD50 for botulinum toxin type A. Moyer E et al., *Botulinum Toxin Type B: Experimental and*

Clinical Experience, being chapter 6, pages 71-85 of "Therapy With Botulinum Toxin", edited by Jankovic, J. et al. (1994), Marcel Dekker, Inc. Botulinum toxin apparently binds with high affinity to cholinergic motor neurons, is translocated into the neuron and blocks the release of acetylcholine. Additional uptake can take place through low affinity receptors, as well as by phagocytosis and pinocytosis.

Regardless of serotype, the molecular mechanism of toxin intoxication appears to be similar and to involve at least three steps or stages. In the first step of the process, the toxin binds to the presynaptic membrane of the target neuron through a specific interaction between the heavy chain (the H chain or HC), and a cell surface receptor. The receptor is thought to be different for each type of botulinum toxin and for tetanus toxin. The carboxyl end segment of the HC appears to be important for targeting of the botulinum toxin to the cell surface.

In the second step, the botulinum toxin crosses the plasma membrane of the target cell. The botulinum toxin is first engulfed by the cell through receptor-mediated endocytosis, and an endosome containing the botulinum toxin is formed. The toxin then escapes the endosome into the cytoplasm of the cell. This step is thought to be mediated by the amino end segment of the HC, the HN, which triggers a conformational change of the toxin in response to a pH of about 5.5 or lower. Endosomes are known to possess a proton pump which decreases intra-endosomal pH. The conformational shift exposes hydrophobic residues in the toxin, which permits the botulinum toxin to embed itself in the endosomal membrane. The botulinum toxin (or at least the light chain of the botulinum) then translocates through the endosomal membrane into the cytoplasm.

The last step of the mechanism of botulinum toxin activity appears to involve reduction of the disulfide bond joining the heavy chain, H chain, and the light chain, L chain. The entire toxic activity of botulinum and tetanus toxins is contained in the L chain of the holotoxin; the L chain is a zinc (Zn++) endopeptidase which selectively cleaves proteins essential for recognition and docking of neurotransmitter-containing vesicles with the cytoplasmic surface of the plasma membrane, and fusion of the vesicles with the plasma membrane. Tetanus neurotoxin, botulinum toxin types B, D, F and G cause degradation of synaptobrevin (also called vesicle-associated membrane protein (VAMP)), a synaptosomal membrane protein. Most of the VAMP present at the cytoplasmic surface of the synaptic vesicle is removed as a result of any one of these cleavage events. Botulinum toxin serotype A and E cleave SNAP-25. Botulinum toxin serotype C1 was originally thought to cleave syntaxin, but was found to cleave syntaxin and SNAP-25. Each of the botulinum toxins specifically cleaves a different bond, except botulinum toxin type B (and tetanus toxin) which cleave the same bond. Each of these cleavages block the process of vesicle-membrane docking, thereby preventing exocytosis of vesicle content.

Botulinum toxins have been used in clinical settings for the treatment of neuromuscular disorders characterized by hyperactive skeletal muscles (i.e. motor disorders). In 1989, a botulinum toxin type A complex was approved by the U.S. Food and Drug Administration for the treatment of blepharospasm, strabismus and hemifacial spasm. Subsequently, a botulinum toxin type A was also approved by the FDA for the treatment of cervical dystonia and for the treatment of glabellar lines, and a botulinum toxin type B was approved for the treatment of cervical dystonia. Non-type A botulinum toxin serotypes apparently have a lower potency and/or a shorter duration of activity as compared to botulinum toxin type A. Clinical effects of peripheral intramuscular botulinum toxin type A are usually seen within one week of injection. The typical duration of symptomatic relief from a single intramuscular injection of botulinum toxin type A averages about three months, although significantly longer periods of therapeutic activity have been reported.

Although all the botulinum toxins serotypes apparently inhibit release of the neurotransmitter acetylcholine at the neuromuscular junction, they do so by affecting different neurosecretory proteins and/or cleaving these proteins at different sites. For example, botulinum types A and E both cleave the 25 kiloDalton (kD) synaptosomal associated protein (SNAP-25), but they target different amino acid sequences within this protein. Botulinum toxin types B, D, F and G act on vesicle-associated protein (VAMP, also called synaptobrevin), with each serotype cleaving the protein at a different site. Finally, botulinum toxin type C1 has been shown to cleave both syntaxin and SNAP-25. These differences in mechanism of action may affect the relative potency and/or duration of action of the various botulinum toxin serotypes. Apparently, a substrate for a botulinum toxin can be found in a variety of different cell types. See e.g. *Biochem J* 1; 339 (pt 1):159-65:1999, and *Mov Disord*, 10(3):376: 1995 (pancreatic islet B cells contains at least SNAP-25 and synaptobrevin).

The molecular weight of the botulinum toxin protein molecule, for all seven of the known botulinum toxin serotypes, is about 150 kD. Interestingly, the botulinum toxins are released by Clostridial bacterium as complexes comprising the 150 kD botulinum toxin protein molecule along with associated non-toxin proteins. Thus, the botulinum toxin type A complex can be produced by Clostridial bacterium as 900 kD, 500 kD and 300 kD forms. Botulinum toxin types B and C1 is apparently produced as only a 700 kD or 500 kD complex. Botulinum toxin type D is produced as both 300 kD and 500 kD complexes. Finally, botulinum toxin types E and F are produced as only approximately 300 kD complexes. The complexes (i.e. molecular weight greater than about 150 kD) are believed to contain a non-toxin hemagglutinin proteins and a non-toxin and non-toxic nonhemagglutinin protein. These two non-toxin proteins (which along with the botulinum toxin molecule comprise the relevant neurotoxin complex) may act to provide stability against denaturation to the botulinum toxin molecule and protection against digestive acids when a botulinum toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine (Habermann E., et al., *Tetanus Toxin and Botulinum A and C Neurotoxins Inhibit Noradrenaline Release From Cultured Mouse Brain*, J Neurochem 51(2); 522-527:1988) CGRP, substance P and glutamate (Sanchez-Prieto, J., et al., *Botulinum Toxin A Blocks Glutamate Exocytosis From Guinea Pig Cerebral Cortical Synaptosomes*, Eur J. Biochem 165; 675-681:1897. Thus, when adequate concentrations are used, stimulus-evoked release of most neurotransmitters can be blocked by botulinum toxin. See e.g. Pearce, L. B., *Pharmacologic Characterization of Botulinum Toxin For Basic Science and Medicine*, Toxicon 35(9); 1373-1412 at 1393; Bigalke H., et al., *Botulinum A Neurotoxin Inhibits Non-Cholinergic Synaptic Transmission in Mouse Spinal Cord Neurons in Culture*, Brain Research 360; 318-324:1985; Habermann E., *Inhibition by Tetanus and Botulinum A Toxin of the release of [3H]Noradrenaline and [3H]GABA From Rat Brain Homogenate*, Experientia 44; 224-226:1988, Bigalke H., et al., *Tetanus Toxin and Botulinum A Toxin Inhibit Release and Uptake of Various Transmitters, as Studied with Particulate Preparations From Rat Brain and Spinal Cord*, Naunyn-Schmiedeberg's Arch Pharmacol 316; 244-251:1981, and; Jankovic J. et al., *Therapy With Botulinum Toxin*, Marcel Dekker, Inc., (1994), page 5.

Botulinum toxin type A can be obtained by establishing and growing cultures of *Clostridium botulinum* in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes C1, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for the known significantly lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy. Additionally, it is known that botulinum toxin type B has, upon intramuscular injection, a shorter duration of activity and is also less potent than botulinum toxin type A at the same dose level.

High quality crystalline botulinum toxin type A can be produced from the Hall A strain of *Clostridium botulinum* with characteristics of $\geq 3 \times 10^7$ U/mg, an A260/A278 of less than 0.60 and a distinct pattern of banding on gel electrophoresis. The known Shantz process can be used to obtain crystalline botulinum toxin type A, as set forth in Shantz, E. J., et al, *Properties and use of Botulinum toxin and Other Microbial Neurotoxins in Medicine*, Microbiol Rev. 56; 80-99:1992. Generally, the botulinum toxin type A complex can be isolated and purified from an anaerobic fermentation by cultivating *Clostridium botulinum* type A in a suitable medium. The known process can also be used, upon separation out of the non-toxin proteins, to obtain pure botulinum toxins, such as for example: purified botulinum toxin type A with an approximately 150 kD molecular weight with a specific potency of $1-2 \times 10^8$ LD50 U/mg or greater; purified botulinum toxin type B with an approximately 156 kD molecular weight with a specific potency of $1-2 \times 10^8$ LD50 U/mg or greater, and; purified botulinum toxin type F with an approximately 155 kD molecular weight with a specific potency of $1-2 \times 10^7$ LD50 U/mg or greater.

Botulinum toxins and/or botulinum toxin complexes can be obtained from List Biological Laboratories, Inc., Campbell, Calif.; the Centre for Applied Microbiology and Research, Porton Down, U.K.; Wako (Osaka, Japan), Metabiologics (Madison, Wis.) as well as from Sigma Chemicals of St Louis, Mo. Pure botulinum toxin can also be used to prepare a pharmaceutical composition.

As with enzymes generally, the biological activities of the botulinum toxins (which are intracellular peptidases) is dependant, at least in part, upon their three dimensional conformation. Thus, botulinum toxin type A is detoxified by heat, various chemicals surface stretching and surface drying. Additionally, it is known that dilution of a botulinum toxin complex obtained by the known culturing, fermentation and purification to the much, much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the botulinum toxin may be used months or years after the toxin containing pharmaceutical composition is formulated, the toxin can be stabilized with a stabilizing agent such as albumin and gelatin.

A commercially available botulinum toxin containing pharmaceutical composition is sold under the trademark BOTOX® (available from Allergan, Inc., of Irvine, Calif.). BOTOX® consists of a purified botulinum toxin type A complex, albumin and sodium chloride packaged in sterile, vacuum-dried form. The botulinum toxin type A is made from a culture of the Hall strain of *Clostridium botulinum* grown in a medium containing N-Z amine and yeast extract. The botulinum toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. The vacuum-dried product is stored in a freezer at or below −5° C. BOTOX® can be reconstituted with sterile, non-preserved saline prior to intramuscular injection. Each vial of BOTOX® contains about 100 units (U) of *Clostridium botulinum* toxin type A purified neurotoxin complex, 0.5 milligrams of human serum albumin and 0.9 milligrams of sodium chloride in a sterile, vacuum-dried form without a preservative.

To reconstitute vacuum-dried BOTOX®, sterile normal saline without a preservative; (0.9% Sodium Chloride Injection) is used by drawing up the proper amount of diluent in the appropriate size syringe. Since BOTOX® may be denatured by bubbling or similar violent agitation, the diluent is gently injected into the vial. For sterility reasons BOTOX® is preferably administered within four hours after the vial is removed from the freezer and reconstituted. During these four hours, reconstituted BOTOX® can be stored in a refrigerator at about 2° C. to about 8° C. Reconstituted, refrigerated BOTOX® has been reported to retain its potency for at least about two weeks. *Neurology*, 48:249-53:1997.

It has been reported that botulinum toxin type A has been used in clinical settings as follows:
(1) about 75-125 units of BOTOX® per intramuscular injection (multiple muscles) to treat cervical dystonia;

(2) 5-10 units of BOTOX® per intramuscular injection to treat glabellar lines (brow furrows) (5 units injected intramuscularly into the procerus muscle and 10 units injected intramuscularly into each corrugator supercilii muscle);

(3) about 30-80 units of BOTOX® to treat constipation by intrasphincter injection of the puborectalis muscle;

(4) about 1-5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.

(5) to treat strabismus, extraocular muscles have been injected intramuscularly with between about 1-5 units of BOTOX®, the amount injected varying based upon both the size of the muscle to be injected and the extent of muscle paralysis desired (i.e. amount of diopter correction desired).

(6) to treat upper limb spasticity following stroke by intramuscular injections of BOTOX® into five different upper limb flexor muscles, as follows:
(a) flexor digitorum profundus: 7.5 U to 30 U
(b) flexor digitorum sublimis: 7.5 U to 30 U
(c) flexor carpi ulnaris: 10 U to 40 U
(d) flexor carpi radialis: 15 U to 60 U
(e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.

(7) to treat migraine, pericranial injected (injected symmetrically into glabellar, frontalis and temporalis muscles) injection of 25 U of BOTOX® has showed significant benefit as a prophylactic treatment of migraine compared to vehicle as measured by decreased measures of migraine frequency, maximal severity, associated vomiting and acute medication use over the three month period following the 25 U injection.

It is known that botulinum toxin type A can have an efficacy for up to 12 months (*European J. Neurology* 6 (Suppl 4): S111-S1150:1999), and in some circumstances for as long as 27 months, when used to treat glands, such as in the treatment of hyperhidrosis. See e.g. Bushara K., *Botulinum toxin and rhinorrhea*, Otolaryngol Head Neck Surg 1996; 114(3):507, and *The Laryngoscope* 109:1344-1346:1999. However, the usual duration of an intramuscular injection of Botox® is typically about 3 to 4 months.

The success of botulinum toxin type A to treat a variety of clinical conditions has led to interest in other botulinum toxin serotypes. Two commercially available botulinum type A preparations for use in humans are BOTOX® available from Allergan, Inc., of Irvine, Calif., and Dysport® available from Beaufour Ipsen, Porton Down, England. A botulinum toxin type B preparation (MyoBloc®) is available from Elan Pharmaceuticals of San Francisco, Calif.

In addition to having pharmacologic actions at the peripheral location, botulinum toxins may also have inhibitory effects in the central nervous system. Work by Weigand et al, *Naunyn-Schmiedeberg's Arch. Pharmacol.* 1976; 292, 161-165, and Habermann, *Naunyn-Schmiedeberg's Arch. Pharmacol.* 1974; 281, 47-56 showed that botulinum toxin is able to ascend to the spinal area by retrograde transport. As such, a botulinum toxin injected at a peripheral location, for example intramuscularly, may be retrograde transported to the spinal cord.

U.S. Pat. No. 5,989,545 discloses that a modified clostridial neurotoxin or fragment thereof, preferably a botulinum toxin, chemically conjugated or recombinantly fused to a particular targeting moiety can be used to treat pain by administration of the agent to the spinal cord.

It has been reported that use of a botulinum toxin to treat various spasmodic muscle conditions can result in reduced depression and anxiety, as the muscle spasm is reduced. Murry T., et al., *Spasmodic dysphonia; emotional status and botulinum toxin treatment*, Arch Otolaryngol 1994 March; 120(3): 310-316; Jahanshahi M., et al., *Psychological functioning before and after treatment of torticollis with botulinum toxin*, J Neurol Neurosurg Psychiatry 1992; 55(3): 229-231. Additionally, German patent application DE 101 50 415 A1 discusses intramuscular injection of a botulinum toxin to treat depression and related affective disorders.

A botulinum toxin has also been proposed for or has been used to treat skin wounds (U.S. Pat. No. 6,447,787), various autonomic nerve dysfunctions (U.S. Pat. No. 5,766,605), tension headache, (U.S. Pat. No. 6,458,365), migraine headache pain (U.S. Pat. No. 5,714,468), sinus headache (U.S. patent application serial number 429069), post-operative pain and visceral pain (U.S. Pat. No. 6,464,986), neuralgia pain (U.S. patent application Ser. No. 630,587), hair growth and hair retention (U.S. Pat. No. 6,299,893), dental related ailments (U.S. provisional patent application Ser. No. 60/418,789), fibromyalgia (U.S. Pat. No. 6,623,742), various skin disorders (U.S. patent application Ser. No. 10/731, 973), motion sickness (U.S. patent application Ser. No. 752,869), psoriasis and dermatitis (U.S. Pat. No. 5,670,484), injured muscles (U.S. Pat. No. 6,423,319) various cancers (U.S. Pat. No. 6,139,845), smooth muscle disorders (U.S. Pat. No. 5,437,291), down turned mouth corners (U.S. Pat. No. 6,358,917), nerve entrapment syndromes (U.S. patent application 2003 0224019), various impulse disorders (U.S. patent application Ser. No. 423,380), acne (WO 03/011333) and neurogenic inflammation (U.S. Pat. No. 6,063,768). Controlled release toxin implants are known (see e.g. U.S. Pat. Nos. 6,306,423 and 6,312,708) as is transdermal botulinum toxin administration (U.S. patent application Ser. No. 10/194,805).

Botulinum toxin type A has been used to treat epilepsia partialis continua, a type of focal motor epilepsy. Bhattacharya K., et al., *Novel uses of botulinum toxin type A: two case reports*, Mov Disord 2000; 15(Suppl 2):51-52.

It is known that a botulinum toxin can be used to: weaken the chewing or biting muscle of the mouth so that self inflicted wounds and resulting ulcers can heal (Payne M., et al, *Botulinum toxin as a novel treatment for self mutilation in Lesch-Nyhan syndrome*, Ann Neurol 2002 September; 52(3 Supp 1):S157); permit healing of benign cystic lesions or tumors (Blugerman G., et al., *Multiple eccrine hidrocystomas: A new therapeutic option with botulinum toxin*, Dermatol Surg 2003 May; 29(5):557-9); treat anal fissure (Jost W., *Ten years' experience with botulinum toxin in anal fissure*, Int J Colorectal Dis 2002 September; 17(5):298-302, and; treat certain types of atopic dermatitis (Heckmann M., et al., *Botulinum toxin type A injection in the treatment of lichen simplex: An open pilot study*, J Am Acad Dermatol 2002 April; 46(4):617-9).

Additionally, a botulinum toxin may have an effect to reduce induced inflammatory pain in a rat formalin model. Aoki K., et al, *Mechanisms of the antinociceptive effect of subcutaneous Botox: Inhibition of peripheral and central nociceptive processing*, Cephalalgia 2003 September; 23(7): 649. Furthermore, it has been reported that botulinum toxin nerve blockage can cause a reduction of epidermal thickness. Li Y, et al., *Sensory and motor denervation influences epidermal thickness in rat foot glabrous skin*, Exp Neurol 1997; 147:452-462 (see page 459). Finally, it is known to administer a botulinum toxin to the foot to treat excessive foot sweating (Katsambas A., et al., *Cutaneous diseases of* the foot: Unapproved treatments, Clin Dermatol 2002 November-December; 20(6):689-699; Sevim, S., et al., *Botulinum toxin—A therapy for palmar and plantar hyperhidrosis*, Acta Neurol Belg 2002 December; 102(4):167-70), spastic toes (Suputtitada, A., *Local botulinum toxin type A injections in the treatment of spastic toes*, Am J Phys Med Rehabil 2002 October; 81(10):770-5), idiopathic toe walking (Tacks, L., et al., *Idiopathic toe walking: Treatment with botulinum toxin A injection*, Dev Med Child Neurol 2002; 44(Suppl 91):6), and foot dystonia (Rogers J., et al., *Injections of botulinum toxin A in foot dystonia*, Neurology 1993 April; 43(4 Suppl 2)).

Tetanus toxin, as wells as derivatives (i.e. with a nonnative targeting moiety), fragments, hybrids and chimeras thereof can also have therapeutic utility. The tetanus toxin bears many similarities to the botulinum toxins. Thus, both the tetanus toxin and the botulinum toxins are polypeptides made by closely related species of *Clostridium* (*Clostridium tetani* and *Clostridium botulinum*, respectively). Additionally, both the tetanus toxin and the botulinum toxins are dichain proteins composed of a light chain (molecular weight about 50 kD) covalently bound by a single disulfide bond to a heavy chain (molecular weight about 100 kD). Hence, the molecular weight of tetanus toxin and of each of the seven botulinum toxins (non-complexed) is about 150 kD. Furthermore, for both the tetanus toxin and the botulinum toxins, the light chain bears the domain which exhibits intracellular biological (protease) activity, while the heavy chain comprises the receptor binding (immunogenic) and cell membrane translocational domains.

Further, both the tetanus toxin and the botulinum toxins exhibit a high, specific affinity for ganglioside receptors on the surface of presynaptic cholinergic neurons. Receptor mediated endocytosis of tetanus toxin by peripheral cholinergic neurons results in retrograde axonal transport, blocking of the release of inhibitory neurotransmitters from central synapses and a spastic paralysis. Contrarily, receptor mediated endocytosis of botulinum toxin by peripheral cholinergic neurons results in little if any retrograde transport, inhibition of acetylcholine exocytosis from the intoxicated peripheral motor neurons and a flaccid paralysis.

Finally, the tetanus toxin and the botulinum toxins resemble each other in both biosynthesis and molecular architecture. Thus, there is an overall 34% identity between the protein sequences of tetanus toxin and botulinum toxin type A, and a sequence identity as high as 62% for some functional domains. Binz T. et al., *The Complete Sequence of Botulinum Neurotoxin Type A and Comparison with Other Clostridial Neurotoxins*, J Biological Chemistry 265(16); 9153-9158:1990.

Acetylcholine

Typically only a single type of small molecule neurotransmitter is released by each type of neuron in the mammalian nervous system, although there is evidence which suggests that several neuromodulators can be released by the same neuron. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the bag 1 fibers of the muscle spindle fiber, by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic as most of the postganglionic neurons of the sympathetic nervous system secret the neurotransmitter norepinephrine. In most instances acetylcholine has an excitatory effect. However, acetylcholine is known to have inhibitory effects at some of the peripheral parasympathetic nerve endings, such as inhibition of heart rate by the vagal nerve.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since, the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic, neurons of the parasympathetic nervous system as well as in those stimulated by the postganglionic cholinergic neurons of the sympathetic nervous system. The nicotinic receptors are found in the adrenal medulla, as well as within the autonomic ganglia, that is on the cell surface of the postganglionic neuron at the synapse between the preganglionic and postganglionic neurons of both the sympathetic and parasympathetic systems. Nicotinic receptors are also found in many nonautonomic nerve endings, for example in the membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as, adrenal medulla (as well as the PC12 cell line) and pancreatic islet cells release catecholamines and parathyroid hormone, respectively, from large dense-core vesicles. The PC12 cell line is a clone of rat pheochromocytoma cells extensively used as a tissue culture model for studies of sympathoadrenal development. Botulinum toxin inhibits the release of both types of compounds from both types of cells in vitro, permeabilized (as by electroporation) or by direct injection of the toxin into the denervated cell. Botulinum toxin is also known to block release of the neurotransmitter glutamate from cortical synaptosomes cell cultures.

A neuromuscular junction is formed in skeletal muscle by the proximity of axons to muscle cells. A signal transmitted through the nervous system results in an action potential at the terminal axon, with activation of ion channels and resulting release of the neurotransmitter acetylcholine from intraneuronal synaptic vesicles, for example at the motor endplate of the neuromuscular junction. The acetylcholine crosses the extracellular space to bind with acetylcholine receptor proteins on the surface of the muscle end plate. Once sufficient binding has occurred, an action potential of the muscle cell causes specific membrane ion channel changes, resulting in muscle cell contraction. The acetylcholine is then released from the muscle cells and metabolized by cholinesterases in the extracellular space. The metabolites are recycled back into the terminal axon for reprocessing into further acetylcholine.

What is needed therefore is a method for effectively treating neuropsychiatric and/or neurological disorders, such as a thalamically mediated disorders, by peripheral administration of a pharmaceutical.

SUMMARY

The present invention meets this need and provides medicaments and methods for effectively treating neuropsychiatric and/or neurological disorders, such as thalamically mediated disorders by peripherally administering a botulinum toxin.

The following definitions apply herein.

"About" means approximately or nearly and in the context of a numerical value or range set forth herein means±10% of the numerical value or range recited or claimed.

"Intramuscular" or "intramuscularly" means into or within (as in administration or injection of a botulinum toxin into) a striated or voluntary muscle, and excludes into or within a smooth or involuntary muscle.

"Locally administering" means directly administering a pharmaceutical at or to the vicinity of a site on or within an animal body, at which site a biological effect of the pharmaceutical is desired. Locally administering excludes systemic routes of administration, such as intravenous or oral administration.

A "neurological (or neurologic) disorder" is a central nervous system malfunction such as epilepsy, chronic pain due to central sensitization, central post stroke pain, regional pain syndrome and phantom limb pain. A neurological disorder includes a brain cortical disfunction which is mediated by or influenced by input to the cortex from the thalamus.

"Neuropsychiatric disorder" means a neurological disturbance that is typically labeled according to which of the four mental faculties are affected, and includes as well any centrally mediated disorder such as CNS generated pain (i.e. allodynia) and a movement disorder, such as epilepsy.

"Peripherally administering" or "peripheral administration" means subdermal, intradermal, transdermal, or subcutaneous administration, but excludes intramuscular administration. "Peripheral" means in a subdermal location, and excludes visceral sites.

"Trigeminal sensory nerve" means a peripheral, afferent nerve cell of the trigeminal nerve which receives or which transmits sensory signals or information from the periphery to a location within a human brain such as the brain stem, thalamus or cortex. Trigeminal sensory nerve therefore excludes trigeminal motor (efferent) nerves. Thus, trigeminal sensory nerves include the trigeminal nerve ophthalmic division, maxillary division, mandibular division, frontal branch, supra orbital nerve, supra trochlear nerve, infraorbital nerve, lacrimal nerve, nasociliary nerve, superior alveolar nerve, buccal nerve, lingual nerve, inferior alveolar nerve, mental nerve, and auriculotemporal nerve.

In accordance with the present invention, a medicament and a method is provided for preventing or for treating a chronic neurological disorder, such as a thalamically mediated disorder. In some embodiments, the medicament can comprise a botulinum toxin for contacting to one or more trigeminal sensory nerves of a patient, thereby preventing or treating a chronic neurological disorder, such as the thalamically mediated disorder. In some embodiments, the botulinum toxin is administered peripherally to a trigeminal sensory nerve or to a vicinity of a trigeminal nerve such that the botulinum toxin contacts the trigeminal nerve. Non-limiting examples of trigeminal sensory nerves include an ophthalmic nerve, maxillary nerve, mandibular nerve, frontal branch, supra orbital nerve, supra trochlear nerve, lacrimal nerve, nasociliary nerve, infraorbital nerve, superior alveolar nerve, buccal nerve, lingual nerve, inferior alveolar nerve, mental nerve or auriculotemporal nerve.

Further in accordance with the present invention, the method comprises contacting a trigeminal nerve and further contacting a spinal nerve that sends afferent fibres to a thalamus. In some embodiments, the botulinum toxin is administered peripherally to a sensory nerve or to a vicinity of a sensory nerve such that the botulinum toxin contacts the sensory nerve. Non-limiting examples of a spinal nerve include a lesser occipital nerve or a greater occipital nerve.

Still further in accordance with the present invention, a medicament within the scope of the present invention can be effective to prevent or treat thalamically mediated or influenced disorders such as epilepsy, chronic pain, or both. Non-limiting examples of chronic pain is central sensitization chronic pain, central post stroke pain, regional pain, phantom limb pain, or demyelinating disease pain.

In some embodiments, the botulinum toxin is administered subcutaneously, intradermally or subdermally. In some embodiments, about 1 unit to about 3000 units of a botulinum toxin are administered to each nerve. In some embodiments, about 1 unit to about 100 units of a botulinum toxin is administered to each nerve.

Methods and medicaments for treating neuropsychiatric disorders according to my invention can comprise a botulinum toxin for peripherally administering to a patient. The botulinum neurotoxin is administered in a therapeutically effective amount to alleviate at least one symptom of a neuropsychiatric disorder. The botulinum neurotoxin may alleviate symptoms associated with the neuropsychiatric disorder by reducing secretions of neurotransmitter from neurons exposed to the botulinum neurotoxin.

A suitable botulinum neurotoxin for use in a method according to my invention can be a neurotoxin made by a bacterium, for example, the neurotoxin may be made from a *Clostridium botulinum, Clostridium butyricum*, or *Clostridium baratii*. The botulinum toxin may be a botulinum toxin type A, type B, type $C_1$, type D, type E, type F, or type G. The botulinum toxin can be administered in an amount of between about $10^{-3}$ U/kg and about 20 U/kg. "U/kg" is an abbreviation for units per kilogram of patient weight. The effects of the botulinum toxin can persist for between about 1 month and 5 years, and can be permanent, that provide a cure for a neuropsychiatric disorder.

Botulinum neurotoxins suitable for use in the include invention include naturally produced as well recombinantly made botulinum neurotoxins, such as botulinum toxins produced by *E. coli*. In addition or alternatively, the neurotoxin can be a modified neurotoxin, that is a neurotoxin which has at least one of its amino acids deleted, modified or replaced, as compared to a native or the modified neurotoxin can be a recombinant produced neurotoxin or a derivative or fragment thereof. The neurotoxins are still able to inhibit a neurotransmitter release.

The botulinum neurotoxin is administered through a peripheral route and thereby to a site within the brain that is believed to be involved in the neuropsychiatric disorder being treated. Alternately, the botulinum neurotoxin can act to reduce peripheral sensory input to a brain location. The botulinum neurotoxin can be peripherally administered so as to reduce afferent (sensory) input to, for example, a lower brain region, the pontine region, the pedunculopontine nucleus, the locus coeruleus, or to the ventral tegmental area, for example. The botulinum neurotoxin can alleviate the symptom that is associated with or dependant upon a neurotransmitter release. The botulinum neurotoxin may also restore a balance between two neuronal systems to alleviate a neuropsychiatric disorder. The botulinum neurotoxin administered to the patient can inhibit acetylcholine release from cholinergic neurons, and can potentially inhibit dopamine release from dopaminergic neurons, and release of norepinephrine from noradrenergic neurons.

The neuropsychiatric disorders treated in accordance with the methods disclosed herein include, and are not limited to, schizophrenia, Alzheimer's disease, mania, and anxiety. The botulinum neurotoxin can alleviate a positive symptom associated with the neuropsychiatric disorder, for example schizophrenia, and can begin alleviate the symptoms within a few hours to up to several (two) weeks after administration.

I have found that a botulinum toxin, such as botulinum toxin type A, can be peripherally administered in amounts between about $10^{-4}$ U/kg and about 20 U/kg to alleviate a neuropsychiatric disorder experienced by a human patient. Preferably, the botulinum toxin used is peripherally administered in an amount of between about $10^{-3}$ U/kg and about 1 U/kg. Most preferably, the botulinum toxin is administered in an amount of between about 0.1 unit and about 10 units. Significantly, the neuropsychiatric disorder alleviating effect of the present disclosed methods can persist for between about 2 months to about 6 months when administration is of aqueous solution of the neurotoxin, and for up to about five years when the neurotoxin is administered as a controlled release implant.

A particular amount of a botulinum neurotoxin administered according to a method within the scope of the disclosed invention can vary according to the particular characteristics of the neuropsychiatric disorder being treated, including its severity and other various patient variables including size, weight, age, and responsiveness to therapy. To guide the practitioner, typically, no less than about 1 unit and no more than about 50 units of a botulinum toxin type A (such as BOTOX®) is administered per injection site, per patient treatment session. For a botulinum toxin type A such as DYSPORT®, no less than about 2 units and no more about 200 units of the botulinum toxin type A are administered per administration or injection site, per patient treatment session. For a botulinum toxin type B such as MYOBLOC®, no less than about 40 units and no more about 2500 units of the botulinum toxin type B are administered per administer or injection site, per patient treatment session. Less than about 1, 2 or 40 units (of BOTOX®, DYSPORT® and MYOBLOC® respectively) can fail to achieve a desired therapeutic effect, while more than about 50, 200 or 2500 units (of BOTOX®, DYSPORT® and MYOBLOC® respectively) can result in clinically observable and undesired muscle hypotonicity, weakness and/or paralysis.

More preferably: for BOTOX® no less than about 2 units and no more about 20 units of a botulinum toxin type A; for DYSPORT® no less than about 4 units and no more than about 100 units, and; for MYOBLOC®, no less than about 80 units and no more than about 1000 units are, respectively, administered per injection site, per patient treatment session.

Most preferably: for BOTOX® no less than about 5 units and no more about 15 units of a botulinum toxin type A; for DYSPORT® no less than about 20 units and no more than about 75 units, and; for MYOBLOC®, no less than about 200 units and no more than about 750 units are, respectively, administered per injection site, per patient treatment session. It is important to note that there can be multiple injection sites (i.e. a pattern of injections) for each patient treatment session.

My invention can also be used to prevent development of a neuropsychiatric disorder by administering a botulinum toxin to or to the vicinity of a trigeminal sensory nerve of the patient with a propensity to develop a neuropsychiatric disorder, thereby preventing development of the neuropsychiatric disorder. A patient with a propensity to develop a neuropsychiatric disorder is one who shows a genetic (i.e. family history) risk factor or behaviors which though not truly aberrant point to progression towards a neuropsychiatric disorder.

DRAWINGS

The following drawings are presented to assist understanding of aspects and features of the present invention.

DESCRIPTION

Figure 1:
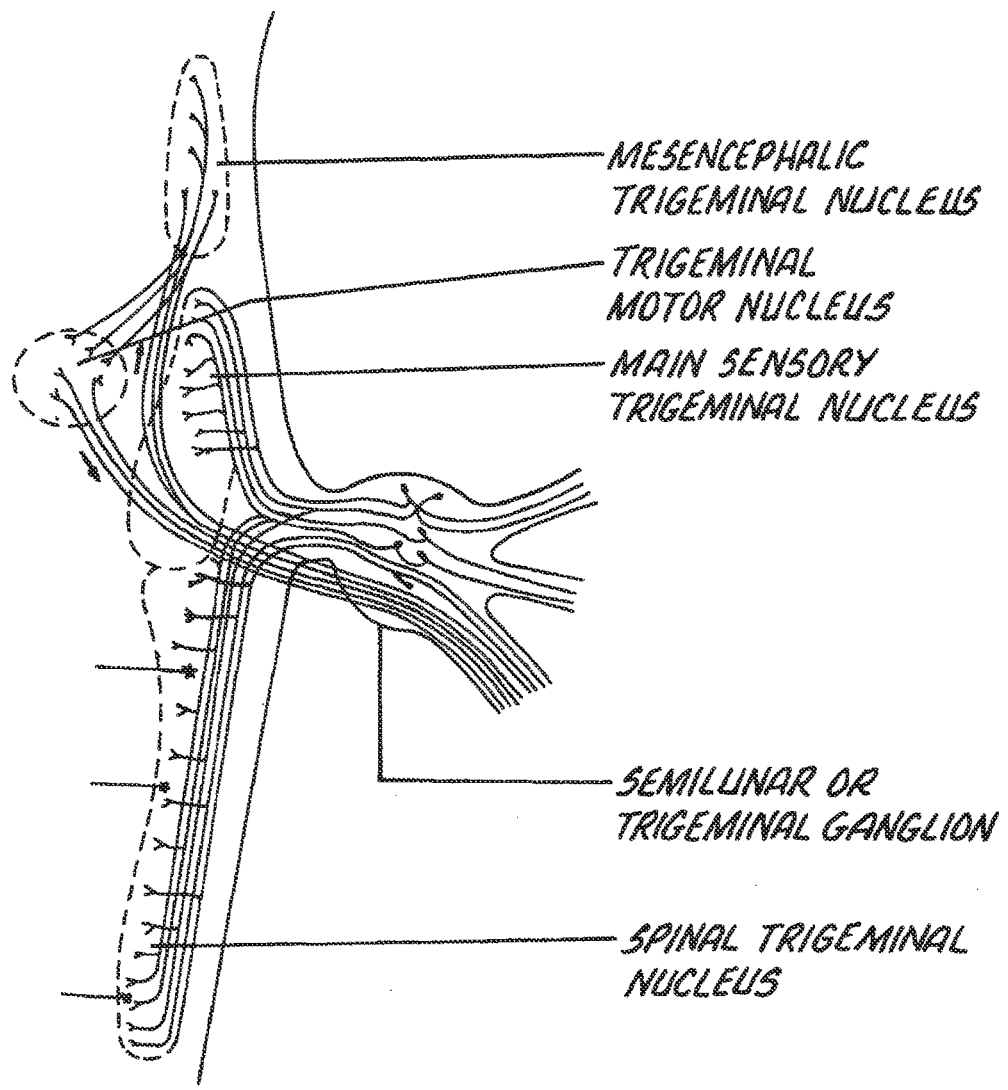
FIG. 1 is a cross sectional dorsal view of the brain stem without the cerebellum, showing locations of trigeminal nuclei.

The present invention is based, in part, upon the discovery that peripheral administration of a botulinum toxin can treat (including alleviate and/or prevent) a variety of neurological disorders, such as a thalamically mediated neurological disorders. Non-limiting examples of thalamically mediated disorders include epilepsy, chronic pain (such as central sensitization chronic pain, central post stroke pain, regional pain, phantom limb pain, or demyelinating disease pain), reflex sympathetic dystrophy, allodynic states; chronic neurological conditions in which kindling is part of the disease process, mood disorders (including bipolar disease) and movement disorders.

In some embodiments of my invention, a botulinum toxin can be administered to prevent development of a neurological disorder (such as a thalamically mediated disorder) in a patient with a propensity to such a disorder. A patient with a propensity to develop a thalamically mediated disorder is one who shows a genetic (e.g., family history) risk factor or behaviors which, though not truly aberrant, point to progression towards a thalamically mediated disorder. In some embodiments, a botulinum toxin is administered to a patient with such propensity prior to the development of a thalamically mediated disorder.

In some embodiments, a botulinum toxin may be administered to treat a patient with a thalamically mediated disorder. A patient is treated when the administered botulinum toxin is effective to relieve the patient from the symptoms of the thalamically mediated disorder for a duration of time. In some embodiments, a patient treated in accordance with the present invention experiences a reduction in the symptoms of the thalamically mediated disorder for more than a day. In some embodiments, a patient treated in accordance with the present invention experiences a reduction in the symptoms of the thalamically mediated disorder for more than a month. In some embodiments, a patient treated in accordance with the present invention experiences a reduction in the symptoms of the thalamically mediated disorder for more than six months.

Without wishing to be bound by theory a physiological mechanism can be set forth to explain the efficacy of the present invention. Thus, it is known that a neurological disorder can be due to a cortical disfunction or dysregulation. A cortical dysregulation, such as an episodic paroxysmal cortical dysregulation, can be influenced by stimulation of the cortex through projections received by the cortex from the thalamus. The thalamus in turn can receive afferent fibres carrying signals (input) from peripheral sensory nerves. Thus, it can be postulated that sensory input from the periphery, to thalamus to cortex can cause or can contribute to genesis of a cortical disfunction. Hence, reduction of a peripheral sensory input to the thalamus can treat a cortical disfunction.

A kindling theory can explain episodes of cortical dysfunction (and an ensuing neurological disorder) occurring over time without or with reduced the peripheral sensory stimulus to the thalamus. Thus, a neurological disorder can be manifested as a cortical disfunction mediated or influenced by thalamic input. A thalamically mediated disorder of the cortex can result in episodic paroxysmal cortical dysregulation, as the cortex is repeatedly stimulated (indirectly) by peripheral sensory nerves that terminate in the thalamus. Over time episodes of cortical dysfunction, and the resulting thalamically mediated disorder, can occur without or with reduced the peripheral sensory stimulus. Such an occurrence of cortical dysfunction without or with a reduced sensory input can be referred to as a kindling effect. For example, it can be postulated that an episode of epilepsy or pain can be induced by repeated peripheral sensory inputs. Thus, over time, the cortex can become kindled, or sensitized, such that future episodes of epilepsy or pain can occur even without or with much less peripheral sensory input to. See Post R M et al., Shared mechanisms in affective illness, epilepsy, and migraine, *Neurology.* 1994; 44 (suppl 7:S37-S47); Goddard G V et al., A permanent change in brain function resulting from daily electrical stimulation, *Exp Neurol.* 1969:25:295-330; Post R M, Transduction of psychosocial stress into the neurobiology of recurrent affective disorder, *AM J Psychiatry,* 1992; 149: 999-1010; and Endicott N A, Psychophysiological correlates of "bipolarity", *J Affect Disord.* 1989; 17:47-56.

Thus, peripheral administration of a botulinum toxin in accordance with the present invention can be carried out to decrease sensory stimulation from the periphery of the central nervous system, and thereby prevents further kindling or reduce the kindling effect upon generation of a neurological disorder, such as thalamically mediated disorder. This desired therapeutic effect of peripheral administration of a botulinum toxin is independent of muscle relaxation. In some embodiments of my invention, the administration of botulinum toxin is not into muscles. Further, the suppressive effect provided by the utilized botulinum toxin can persist for a relatively long period of time, for example, for more than two months, and potentially for several years.

In some embodiments, the botulinum toxin can be administered to and/or around the vicinity of a trigeminal nerve, such that the botulinum toxin contacts the trigeminal nerve, such as a trigeminal sensory nerve. In some embodiments, the botulinum toxin may be administered to and/or around the vicinity of a trigeminal ganglion, such that the botulinum toxin contacts the trigeminal ganglion. In some embodiments, the botulinum toxin can be administered to and/or around the vicinity of a spinal nerve such that the botulinum toxin contacts the spinal nerve, wherein the spinal nerve sends an afferent to or terminates in the thalamus. The term spinal nerve generally refers to the mixed spinal nerve, which is formed from the dorsal and ventral roots that come out of the spinal cord. The spinal nerve is the portion that passes out of the vertebrae through the intervertebral foramen. In some embodiments, the botulinum toxin may be administered to and/or around the vicinity of the trigeminal nerve, to and/or around the trigeminal ganglion, and to and/or around the vicinity of a spinal nerve, wherein the spinal nerve sends an afferent to or terminates in the thalamus.

In some embodiments, a botulinum toxin is administered to and/or around the vicinity of a trigeminal nerve, such that the botulinum toxin contacts the trigeminal nerve. As set forth above, the desired therapeutic effect of peripheral administration of a botulinum toxin can be due to a down regulation of sensory trigeminal input to the cortex. Alternately, the botulinum toxin may exert a direct central effect upon retrograde transports up the trigeminal nerve to the thalamus. For example, it has been demonstrated that peripheral, subcutaneous administration of a botulinum toxin can cause a reduction in the sensitization level of central (dorsal horn) neurons which are anatomically distant from the peripheral botulinum toxin injection site. Aoki K., et al., *Mechanisms of the antinociceptive effect of subcutaneous Botox: Inhibition of peripheral and central nociceptive processing,* Cephalalgia 2003 September; 23(7):649 ABS P3I14; Cui M., et al., *Mechanisms of the antinociceptive effect of subcutaneous Botox: Inhibition of peripheral and central nociceptive processing,* Naunyn Schmiedebergs Arch Pharmacol 2002; 365 (Suppl 2):R17.

Thus, once present in the thalamus, the botulinum toxin can act can decrease the ability of the thalamic neurons to stimulate the cortex, and thereby treat a thalamically mediated disorder. Hence, administration of a botulinum toxin according to the present invention can be effective to reduce trigeminal sensory stimulation in the thalamus, raising a threshold level for neuronal firing at the cortical level, and thereby removing kindling input to the cortex to permit treatment of a neurological disorder, such as a thalamically mediated disorder. See Bolay, H., et al., *Intrinsic brain activity triggers trigeminal meningeal afferents in a migraine model,* Nature Medicine, vol. 8 (2); February 2002: 136-142 (botulinum toxin can be used to change/ameliorate the progression of chronic migraines, and there is evidence for the involvement of the trigeminal nerve in the genesis of migraine headaches); Durham P. et al., *Regulation of calcitonin gene-related peptide secretion from trigeminal nerve cells by botulinum toxin type A: implications for migraine therapy,* Headache 2004 January; 44(1):35-43 (botulinum toxin can be used to treat migraine because of the ability of the botulinum toxin to repress calcitonin gene-related peptide release from trigeminal sensory neurons); and Aoki K., et al, *Evidence for antinociceptive activity of botulinum toxin type A in pain management,* Headache 2003 July; 43(Suppl 1):S9-S15 (There is evidence that a botulinum toxin administered to the region of a sensory nerve, such as a trigeminal nerve, can reduce central sensitization).

Figure 2:
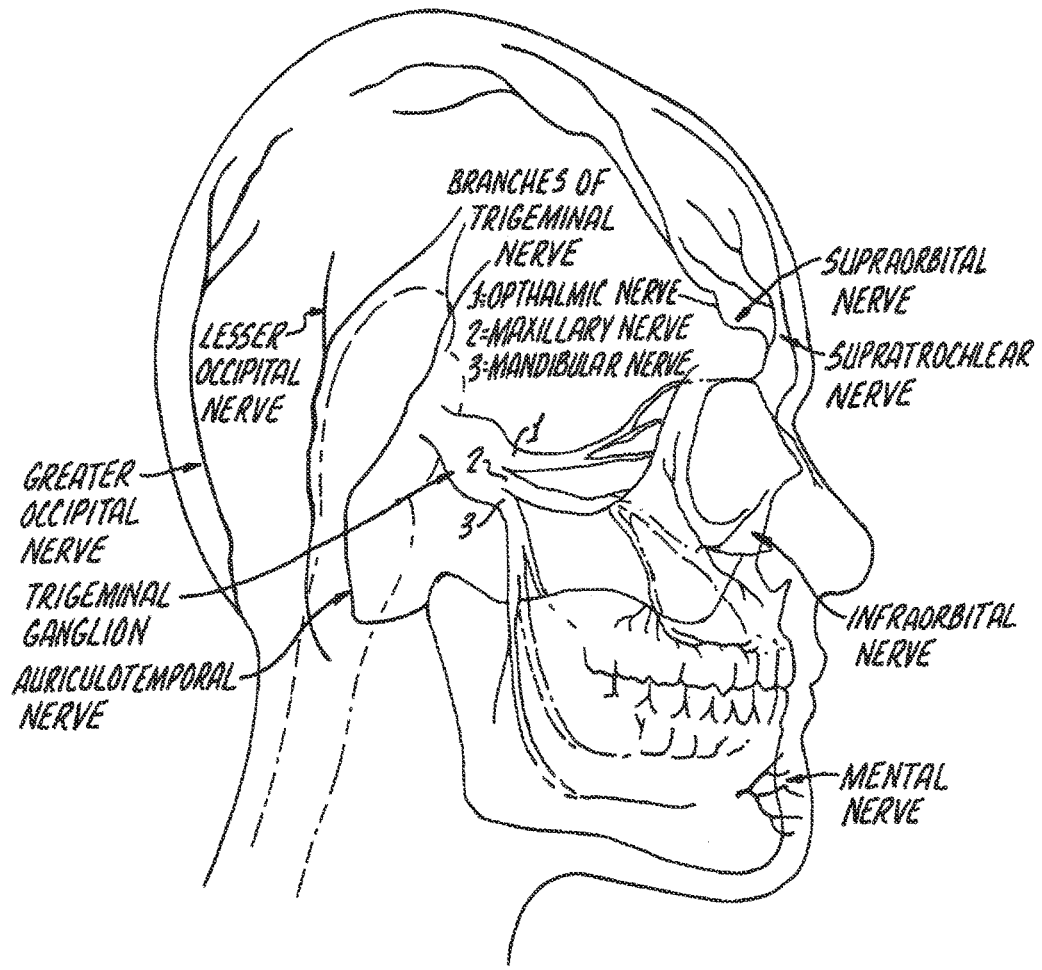
FIG. 2 is a representation of the locations of trigeminal nerves and spinal nerves in a human head.

A botulinum toxin can be administered to and/or around one or more trigeminal nerves. These trigeminal nerves include, and are not limited to, the ophthalmic nerve, maxillary nerve, mandibular nerve, supra orbital nerve, supra trochlear nerve, infraorbital nerve, lacrimal nerve, nasociliary nerve, superior alveolar nerve, buccal nerve, lingual nerve, inferior alveolar nerve, mental nerve, auriculotemporal nerve and frontal branches of the trigeminal nerve. See FIG. 2. In some embodiments, botulinum toxin is administered to only one trigeminal nerve. In some embodiments, botulinum toxin is administered to more than one trigeminal nerve. In some embodiments, botulinum toxin may be administered to the trigeminal nerves simultaneously. In some embodiments, botulinum toxin may be administered to the trigeminal nerves sequentially.

In some embodiments, a botulinum toxin is administered to or around the vicinity of a spinal nerve, wherein the spinal nerve sends an afferent to or terminates in the thalamus. These spinal nerves include, and are not limited to, the lesser occipital nerve and the greater occipital nerve. See FIG. 2. In some embodiments, botulinum toxin is administered to only one spinal nerve. In some embodiments, botulinum toxin is administered to more than one spinal nerve. In some embodiments, botulinum toxin may be administered to the spinal nerves simultaneously. In some embodiments, botulinum toxin may be administered to the spinal nerves sequentially.

In some embodiments, a botulinum toxin is administered to or around the vicinity of one or more trigeminal nerve, and one or more spinal nerve, wherein the spinal nerve sends an afferent to or terminates in the thalamus. In some embodiments, botulinum toxin is administered to the ophthalmic nerve, maxillary nerve, mandibular nerve, supra orbital nerve, supra trochlear nerve, infraorbital nerve, lacrimal nerve, nasociliary nerve, superior alveolar nerve, buccal nerve, lingual nerve, inferior alveolar nerve, mental nerve, auriculotemporal nerve, frontal branch, lesser occipital nerve, and greater occipital nerve. In some embodiments, botulinum toxin is administered to these nerves simultaneously. In some embodiments, botulinum toxin may be administered to these nerves sequentially.

The botulinum toxin can be administered to any region of the nerves indicated herein. In some embodiments, the botulinum toxin is administered to the nerve endings. For example, the botulinum toxin may be administered subcutaneously, intradermally and/or subdermally.

The botulinum toxins used in accordance with the invention can inhibit transmission of chemical or electrical signals between select neuronal groups that are involved in generation, progression and/or maintenance of a thalamically mediated disorder. The botulinum toxins used can inhibit neurotransmission by reducing or preventing exocytosis of a neurotransmitter from particular neurons exposed to the neurotoxin. In some embodiments, the botulinum toxins can reduce neurotransmission by inhibiting the generation of action potentials of particular neurons exposed to the toxin.

Examples of suitable botulinum toxins which may be used to prevent or treat thalamically mediated disorders include botulinum toxins made from *Clostridium* bacteria, such as *Clostridium botulinum*, *Clostridium butyricum* and *Clostridium barati*. The botulinum toxins may be selected from a group of botulinum toxin types A, B, C (e.g., $C_1$), D, E, F, and G. In some embodiments, the botulinum toxin administered to the patient is botulinum toxin type A. Botulinum toxin type A is desirable due to its high potency in humans, ready availability, and known use for the treatment of muscle disorders when administered by intramuscular injection.

In some embodiments, the present invention also includes the use of (a) botulinum toxins obtained or processed by bacterial culturing, toxin extraction, concentration, preservation, freeze drying, and/or reconstitution; and/or (b) modified or recombinant botulinum toxins, that is botulinum toxins that have had one or more amino acids or amino acid sequences deliberately deleted, modified or replaced by known chemical/biochemical amino acid modification procedures or by use of known host cell/recombinant vector recombinant technologies, as well as derivatives or fragments of neurotoxins so made. These botulinum toxin variants should retain the ability to inhibit neurotransmission between or among neurons, and some of these variants may provide increased durations of inhibitory effects as compared to native botulinum toxins, or may provide enhanced binding specificity to the neurons exposed to the botulinum toxins. These botulinum toxin variants may be selected by screening the variants using conventional assays to identify neurotoxins that have the desired physiological effects of inhibiting neurotransmission.

Botulinum toxins suitable for use in the include invention include naturally produced as well recombinantly made botulinum toxins, such as botulinum toxins produced by *E. coli*. In some embodiments, the toxin may be a modified toxin, that is, a neurotoxin which has at least one of its amino acids deleted, modified or replaced, as compared to a native toxin. In some embodiments, the toxin is a chimera toxin.

Botulinum toxins for use according to the present invention can be stored in lyophilized, vacuum dried form in containers under vacuum pressure or as stable liquids. Prior to lyophilization the botulinum toxin can be combined with pharmaceutically acceptable excipients, stabilizers and/or carriers, such as albumin. The lyophilized material can be reconstituted with saline or water to create a solution or composition containing the botulinum toxin to be administered to the patient.

In some embodiments, a composition may only comprise a single type of a botulinum toxin, such as a botulinum toxin type A, as the active ingredient to suppress neurotransmission. In some embodiments, a composition may include two or more types of botulinum toxins, which may provide enhanced therapeutic effects upon a thalamically mediated disorder. For example, a composition administered to a patient may include botulinum toxin type A and botulinum toxin type B. Administering a single composition containing two different botulinum toxins may permit the effective concentration of each of the botulinum toxins to be lower than if a single botulinum toxin is administered to the patient while still achieving the desired therapeutic effects. The composition administered to the patient may also contain other pharmaceutically active ingredients, such as, protein receptor or ion channel modulators, in combination with the botulinum toxin or botulinum toxins. These modulators may contribute to the reduction in neurotransmission between the various neurons. For example, a composition may contain gamma aminobutyric acid (GABA) type A receptor modulators that enhance the inhibitory effects mediated by the $GABA_A$ receptor. The $GABA_A$ receptor inhibits neuronal activity by effectively shunting current flow across the cell membrane. $GABA_A$ receptor modulators may enhance the inhibitory effects of the $GABA_A$ receptor and reduce electrical or chemical signal transmission from the neurons. Examples of $GABA_A$ receptor modulators include benzodiazepines, such as diazepam, oxazepam, lorazepam, prazepam, alprazolam, halazepam, chlordiazepoxide, and clorazepate. Compositions may also contain glutamate receptor modulators that decrease the excitatory effects mediated by glutamate receptors. Examples of glutamate receptor modulators include agents that inhibit current flux through AMPA, NMDA, and/or kainate types of glutamate receptors. The compositions may also include agents that modulate dopamine receptors, such as antipsychotics, norepinephrine receptors, and/or serotonin receptors. The compositions may also include agents that affect ion flux through voltage gated calcium channels, potassium channels, and/or sodium channels. Thus, the compositions used to treat thalamically mediated disorders may include one or more botulinum toxins, in addition to ion channel receptor modulators that can reduce neurotransmission.

In some embodiments, a composition comprising a botulinum toxin is administered peripherally, and a composition containing other pharmaceutical agents, such as antipsychotics, that can cross the blood brain barrier can be administered systemically, such as by intravenous administration, to achieve the desired therapeutic effects.

In some embodiments, the botulinum toxin may be administered to the patient in conjunction with a solution or composition that locally decreases the pH of the target tissue environment. For example, a solution containing hydrochloric acid may be used to locally and temporarily reduce the pH of the target tissue environment to facilitate translocation of the neurotoxin across cell membranes. The reduction in local pH may be desirable when the composition contains fragments of botulinum toxins that may not have a functional targeting moiety (e.g., a portion of the toxin that binds to a neurotoxin receptor), and/or a translocation domain). By way of example, and not by way of limitation, a fragment of a botulinum toxin that comprises the proteolytic domain of the toxin may be administered to the patient in conjunction with an agent that decreases the local pH of the target tissue. Without wishing to be bound by any particular theory, it is believed that the lower pH may facilitate the translocation of the proteolytic domain across the cell membrane so that the neurotoxin fragment can exert its toxic effects within the cell. The pH of the target tissue is only temporarily lowered so that neuronal and/or glial injury is reduced.

Methods of administration include injecting a composition (e.g. a solution) comprising the botulinum toxin as described above. In some embodiments, the method of administration includes implanting a controlled release system that controllably releases the botulinum toxin to the target trigeminal tissue. For example, the botulinum toxin can be administered peripherally using a subdermal implant. Such controlled release systems reduce the need for repeat injections. Diffusion of biological activity of a botulinum toxin within a tissue appears to be a function of dose and can be graduated. Jankovic J., et al *Therapy With Botulinum Toxin*, Marcel Dekker, Inc., (1994), page 150. Thus, diffusion of botulinum toxin can be controlled to reduce potentially undesirable side effects that may affect the patient's cognitive abilities. For example, the botulinum toxin may be administered so that the botulinum toxin primarily effects neural systems believed to be involved in a selected thalamically mediated disorder, and does not have negatively adverse effects on other neural systems.

The present invention is also based upon the discovery that peripheral administration of a botulinum neurotoxin can provide significant and long lasting relief from a variety of different neuropsychiatric disorders.

Without wishing to be bound by theory, peripheral administration of a botulinum toxin according to the methods disclosed herein is believed to permit a botulinum neurotoxin to either be administered (by retrograde progression of the botulinum toxin) to a site within a patient's cranium and/or to reduce afferent, sensory input to a site within the patients' cranium to thereby influence intracranial neurons involved in a neuropsychiatric disorder.

Thus, neuropsychiatric disorders are believed to originate from episodic paroxysmal cortical dysregulation, influenced by various stress factors[1]. Over time these episodes of cortical dysfunction, and the resulting neuropsychiatric disorder, can occur without stressor inputs. Hence a kindling model[2,3] for development of a neuropsychiatric disorder is appropriate. Under a kindling model repeated low levels of stimulation can over time result in occurrence of a neuropsychiatric disorder without further sensory input. It is known that the brain can become kindled or sensitized, such that pathways inside the central nervous system are reinforced and future episodes of, for example, depression, hypomania, mania, bipolar disorder or epilepsy can then occur independently of an outside stimulus with greater and greater frequency. My kindling theory of neuropsychiatric disorders is supported by descriptions states of physiologic responsivity and heightened reactivity[4]. A botulinum toxin can be used to decrease afferent stimulation of the central nervous system and thereby prevent further kindling of a neuropsychiatric disorder.

[1] Post R M, Silberstein S D. Shared mechanisms in affective illness, epilepsy, and migraine. *Neurology.* 1994; 44(suppl 7):S37-S47.
[2] Goddard G V, McIntyre D C, Leech C K, A permanent change in brain function resulting from daily electrical stimulation *Exp Neurol.* 1969; 25:295-330.
[3] Post R M, Transduction of psychosocial stress into the neurobiology of recurrent affective disorder. *AM J Psychiatry,* 1992; 149:999-1010.
[4] Endicott N A Psychophysiological correlates of "bipolarity." *J Affect Disord.* 1989; 17:47-56.

Thus, a neuropsychiatric disorder can be treated by decreasing afferent stimulation of the cortex. In particular, administration of a botulinum toxin to a site or sites around a trigeminal nerve and $c_2/c_3$ afferent the result can be a decreased responsiveness in the nucleus caudalis. This in turn can decrease thalamic and subsequent cortical afferent, sensory input. It is known that $c_2/c_3$ afferents project to the trigeminal complex and are involved with sensitization of $2^{nd}$ and $3^{rd}$ order neurons. Significantly, it has been demonstrated that peripheral, subcutaneous administration of a botulinum toxin can cause a reduction in the sensitization level of central (dorsal horn) neurons which are anatomically distant from the peripheral botulinum toxin injection site. Aoki K., et al., *Mechanisms of the antinociceptive effect of subcutaneous Botox: Inhibition of peripheral and central nociceptive processing*, Cephalalgia 2003 September; 23(7): 649 ABS P3I14; Cui M., et al., *Mechanisms of the antinociceptive effect of subcutaneous Botox: Inhibition of peripheral and central nociceptive processing*, Naunyn Schmiedebergs Arch Pharmacol 2002; 365(Suppl 2):R17.

Thus, a botulinum toxin can be used to treat a neuropsychiatric disorder by blocking the progression of a neuropsychiatric disorder that can occur due to repeated sensory input to the cortex from a peripheral trigeminal sensory nerve. Notably, it has been reported that a botulinum toxin can be used to change (ameliorate) the progression of chronic migraines[5], and there is evidence for the involvement of the trigeminal nerve in the genesis of migraine headaches. Bolay, H., et al., *Intrinsic brain activity triggers trigeminal meningeal afferents in a migraine model*, Nature Medicine, vol. 8 (2); February 2002: 136-142. Additionally, there is evidence that a botulinum toxin can be used to treat migraine because of the ability of the botulinum toxin to repress calcitonin gene-related peptide release from trigeminal sensory neurons. Durham P. et al., *Regulation of calcitonin gene-related peptide secretion from trigeminal nerve cells by botulinum toxin type A: implications for migraine therapy*, Headache 2004 January; 44(1):35-43.

Thus, peripheral administration of a botulinum toxin, by decreasing afferent trigeminal cortical stimulation, can remove external stressors which centrally kindle occurrence of a neuropsychiatric disorder. Conditions that can be treated or attenuated with this approach to reduce cortical sensory input through a trigemino-thalamic route include: central pain syndromes particularly chronic pain syndromes with central sensitization; post stroke pain syndrome; reflex sympathetic dystrophy; phantom limb pain; allodynic states; chronic neurological conditions in which kindling is part of the disease process; epilepsy; neuropsychiatric disorders, including mood disorders, particularly bipolar disease, and movement disorders.

Thus, a method according to my invention uses a botulinum toxin to produce a modulating effect on the central nervous system when administered (i.e. injected) into a trigeminal nerve branch and/or ansa cervicalis branch particularly in the C2 and C3 dermatomes. The trigeminal sensory nerve endings that are targeted include the supra-orbital, supra-trochlear, temporo-auricular, greater and lesser occipital nerves. This method leads to decreased sensory afferents to the spinal tract of the nucleus caudalis and thereby decreased central afferent input to the thalamus and thence to the cortex.

Hence, administration of a botulinum toxin according to my invention is carried out so to achieve a desired central effect, that is the raising of a threshold level for neuronal firing at the cortical level, by reducing trigeminal sensory input and thereby removing kindling input to the cortex. By doing so, a centrally mediated neuropsychiatric disorder can be treated. Thus, the efficacy of the present invention can be due to a reduction of a kindling effect upon the cortex, as a kindling effect reduction results in a slowing down of the progression, or the treating, of a centrally mediated neuropsychiatric disorder.

There is evidence that a botulinum toxin administered to the region of a sensory nerve, such as a trigeminal nerve, can reduce central sensitization. Aoki K., et al, *Evidence for antinociceptive activity of botulinum toxin type A in pain management*, Headache 2003 July; 43(Suppl 1):S9-S15; Durham P., et al., *Regulation of calcitonin gene-related peptide secretion from trigeminal nerve cells by botulinum toxin type A: implications for migraine therapy*, Headache 2004 January; 44(1):35-43.

Thus, decreasing afferent impulses in the trigeminal innervated regions can decrease central afferents initially in the brainstem and subsequently in the thalamus, the sensory cortex, and in the motor cortex. Hence, a neuropsychiatric disorder can be treated by for example, inhibiting a kindling effect, and down regulating sensory input to central afferents.

Input to the caudal segment of the spinal trigeminal nucleus from the cervical plexus branches include the greater and lesser occipital nerves, which travel over the occipital and suboccipital regions. Other nerves include the greater auricular nerve, and the anterior cutaneous nerve of the neck. In a preferred embodiment of my invention a botulinum toxin is administered delivered to these trigeminal nerve branches which run in the dermal region.

The treatment outlined above is expected to down regulate central nervous system activation and reduce kindling over the long-term. This effect is independent of muscle relaxation. Injections need to be in the region of the trigeminal and cervical plexus branches, and not in muscles of the face, neck and head.

The aim of the outlined treatment is to maximize the effects on the cortical homunculus. Using the trigeminal sensory system approach, each unit of a botulinum toxin delivered has the maximum cortical effects on the head/face representation in the homunculus, with the least side effects. This allows for the maximum central effect of each unit of botulinum toxin delivered peripherally.

An alternate theory for the efficacy (therapeutic result) of a method practiced according to the present invention rests upon the fact that a botulinum toxin, can inhibit neuronal exocytosis of several different CNS neurotransmitters, for example acetylcholine. It is known that cholinergic neurons are present throughout the brain. Additionally, cholinergic nuclei exist in the basal ganglia or in the basal forebrain, with projections to cerebral regions involved in emotion, behavior, and other cognitive functions. Thus, target tissues for a method within the scope of the present invention can include neurotoxin induced reversible denervation of brain cholinergic systems, such as basal nuclei or pedunculopontine nucleus. For example, peripheral injection or peripheral implantation of a botulinum neurotoxin to or to the vicinity of a trigeminal nerve can permit the botulinum toxin to be retrograde transported to a cholinergic brain nucleus with the result of (1) downregulation of dopaminergic release from target sites of cholinergic neurons due to the action of the toxin upon cholinergic terminals projecting into the ventral tegmental area from pedunculopontine nucleus; and (2) attenuation of ventral tegmental area output due to the action of the toxin upon cholinergic neurons projecting to the ventral tegmental area.

Alternately, use of a botulinum toxin as set forth herein can inhibit of exocytosis of nonacetylcholine neurotransmitters. For example, it is believed that once the proteolytic domain of a botulinum toxin, is incorporated into a target neuron, the toxin inhibits release of any neurotransmitter from that neuron. Thus, the botulinum neurotoxin can be peripherally administered to a target brain nuclei containing a substantial number of dopaminergic neurons so that the neurotoxin effectively inhibits the release of dopamine from those neurons. Similarly, the botulinum neurotoxin can be administered to other nuclei such as the Raphe nuclei to inhibit serotonin exocytosis, the locus coeruleus nuclei to inhibit norepinephrine exocytosis.

The botulinum neurotoxins used in accordance with the invention disclosed herein can inhibit transmission of chemical or electrical signals between select neuronal groups that are involved in generation, progression and/or maintenance of a neuropsychiatric disorder. The botulinum neurotoxins used, at the dose levels used, are not cytotoxic to the cells that are exposed to the neurotoxin. The botulinum neurotoxins used can inhibit neurotransmission by reducing or preventing exocytosis of a neurotransmitter from particular neurons exposed to the neurotoxin. Alternately, the botulinum neurotoxins can reduce neurotransmission by inhibiting the generation of action potentials of particular neurons exposed to the toxin. The neuropsychiatric disorder suppressive effect provided by the utilized botulinum neurotoxin can persist for a relatively long period of time, for example, for more than two months, and potentially for several years.

Examples of suitable botulinum neurotoxins which can be used to treat neuropsychiatric disorders according to my invention disclosed herein, include botulinum neurotoxins made from *Clostridium* bacteria, such as *Clostridium botulinum, Clostridium butyricum* and *Clostridium baratii*. The botulinum toxins can selected from a group of botulinum toxin types A, B, C, D, E, F, and G. In one embodiment of the invention, the botulinum neurotoxin administered to the patient is botulinum toxin type A. Botulinum toxin type A is desirable due to its high potency in humans, ready availability, and known use for the treatment of muscle disorders when administered by intramuscular injection. The present invention also includes the use of (a) botulinum neurotoxins obtained or processed by bacterial culturing, toxin extraction, concentration, preservation, freeze drying, and/or reconstitution; and/or (b) modified or recombinant botulinum neurotoxins, that is botulinum neurotoxins that have had one or more amino acids or amino acid sequences deliberately deleted, modified or replaced by known chemical/biochemical amino acid modification procedures or by use of known host cell/recombinant vector recombinant technologies, as well as derivatives or fragments of neurotoxins so made. These botulinum neurotoxin variants should retain the ability to inhibit neurotransmission between or among neurons, and some of these variants may provide increased durations of inhibitory effects as compared to native botulinum neurotoxins, or may provide enhanced binding specificity to the neurons exposed to the botulinum neurotoxins. These botulinum neurotoxin variants may be selected by screening the variants using conventional assays to identify neurotoxins that have the desired physiological effects of inhibiting neurotransmission.

Botulinum toxins for use according to the present invention can be stored in lyophilized, vacuum dried form in containers under vacuum pressure or as stable liquids. Prior to lyophilization the botulinum toxin can be combined with pharmaceutically acceptable excipients, stabilizers and/or carriers, such as albumin. The lyophilized material can be reconstituted with saline or water to create a solution or composition containing the botulinum toxin to be administered to the patient.

Although the composition can only contain a single type of a botulinum neurotoxin, such as a botulinum toxin type A, as the active ingredient to suppress neurotransmission, other therapeutic compositions may include two or more types of botulinum neurotoxins, which may provide enhanced therapeutic effects upon a neuropsychiatric disorder. For example, a composition administered to a patient may include botulinum toxin type A and botulinum toxin type B. Administering a single composition containing two different botulinum neurotoxins may permit the effective concentration of each of the botulinum neurotoxins to be lower than if a single botulinum neurotoxin is administered to the patient while still achieving the desired therapeutic effects. The composition administered to the patient may also contain other pharmaceutically active ingredients, such as, protein receptor or ion channel modulators, in combination with the botulinum neurotoxin or botulinum neurotoxins. These modulators may contribute to the reduction in neurotransmission between the various neurons. For example, a composition may contain gamma aminobutyric acid (GABA) type A receptor modulators that enhance the inhibitory effects mediated by the $GABA_A$ receptor. The $GABA_A$ receptor inhibits neuronal activity by effectively shunting current flow across the cell membrane. $GABA_A$ receptor modulators may enhance the inhibitory effects of the $GABA_A$ receptor and reduce electrical or chemical signal transmission from the neurons. Examples of $GABA_A$ receptor modulators include benzodiazepines, such as diazepam, oxazepam, lorazepam, prazepam, alprazolam, halazepam, chlordiazepoxide, and clorazepate. Compositions may also contain glutamate receptor modulators that decrease the excitatory effects mediated by glutamate receptors. Examples of glutamate receptor modulators include agents that inhibit current flux through AMPA, NMDA, and/or kainate types of glutamate receptors. The compositions may also include agents that modulate dopamine receptors, such as antipsychotics, norepinephrine receptors, and/or serotonin receptors. The compositions may also include agents that affect ion flux through voltage gated calcium channels, potassium channels, and/or sodium channels. Thus, the compositions used to treat neuropsychiatric disorders may include one or more botulinum toxins, in addition to ion channel receptor modulators that can reduce neurotransmission.

Preferably, the botulinum neurotoxin is peripherally administered by administering it to or to the vicinity of a trigeminal nerve or to a trigeminal nerve branch or trigeminal ganglion nuclei. This method of administration permit the botulinum neurotoxin to be administered to and/or to affect select intracranial target tissues. Methods of administration include injection of a solution or composition containing the botulinum neurotoxin, as described above, and include implantation of a controlled release system that controllably releases the botulinum neurotoxin to the target trigeminal tissue. Such controlled release systems reduce the need for repeat injections. Diffusion of biological activity of a botulinum toxin within a tissue appears to be a function of dose and can be graduated. Jankovic J., et al *Therapy With Botulinum Toxin*, Marcel Dekker, Inc., (1994), page 150. Thus, diffusion of botulinum toxin can be controlled to reduce potentially undesirable side effects that may affect the patient's cognitive abilities. For example, the botulinum neurotoxin may be administered so that the botulinum neurotoxin primarily effects neural systems believed to be involved in a selected neuropsychiatric disorder, and does not have negatively adverse effects on other neural systems.

In addition, the botulinum neurotoxin may be administered to the patient in conjunction with a solution or composition that locally decreases the pH of the target tissue environment. For example, a solution containing hydrochloric acid may be used to locally and temporarily reduce the pH of the target tissue environment to facilitate translocation of the neurotoxin across cell membranes. The reduction in local pH may be desirable when the composition contains fragments of botulinum neurotoxins that may not have a functional targeting moiety (e.g., a portion of the toxin that binds to a neurotoxin receptor), and/or a translocation domain). By way of example, and not by way of limitation, a fragment of a botulinum toxin that comprises the proteolytic domain of the toxin may be administered to the patient in conjunction with an agent that decreases the local pH of the target tissue. Without wishing to be bound by any particular theory, it is believed that the lower pH may facilitate the translocation of the proteolytic domain across the cell membrane so that the neurotoxin fragment can exert its toxic effects within the cell. The pH of the target tissue is only temporarily lowered so that neuronal and/or glial injury is reduced.

The botulinum neurotoxin is administered peripherally, and a composition containing other pharmaceutical agents, such as antipsychotics, that can cross the blood brain barrier can be administered systemically, such as by intravenous administration, to achieve the desired therapeutic effects.

Implants that are employed in accordance with the present invention may comprise various polymers. For example, a polyanhydride polymer, Gliadel® (Stolle R & D, Inc., Cincinnati, Ohio) a copolymer of poly-carboxyphenoxypropane and sebacic acid in a ratio of 20:80 has been used to make implants, and has been peripherally implanted to treat malignant gliomas. Polymer and BCNU can be co-dissolved in methylene chloride and spray-dried into microspheres. The microspheres can then be pressed into discs 1.4 cm in diameter and 1.0 mm thick by compression molding, packaged in aluminum foil pouches under nitrogen atmosphere and sterilized by 2.2 megaRads of gamma irradiation. The polymer permits release of carmustine over a 2-3 week period, although it can take more than a year for the polymer to be largely degraded. Brem, H., et al, *Placebo-Controlled Trial of Safety and Efficacy of Intraoperative Controlled Delivery by Biodegradable Polymers of Chemotherapy for Recurrent Gliomas*, Lancet 345; 1008-1012:1995.

In some embodiments, implants useful in practicing the methods disclosed herein may be prepared by mixing a desired amount of a stabilized botulinum toxin (such as non-reconstituted BOTOX® or DYSPORT®) into a solution of a suitable polymer dissolved in methylene chloride. The solution may be prepared at room temperature. The solution can then be transferred to a Petri dish and the methylene chloride evaporated in a vacuum desiccator. Depending upon the implant size desired and hence the amount of incorporated neurotoxin, a suitable amount of the dried neurotoxin incorporating implant is compressed at about 8000 p.s.i. for 5 seconds or at 3000 p.s.i. for 17 seconds in a mold to form implant discs encapsulating the neurotoxin. See e.g. Fung L. K. et al., *Pharmacokinetics of Interstitial Delivery of Carmustine 4-Hydroperoxycyclophosphamide and Paclitaxel From a Biodegradable Polymer Implant in the Monkey Brain*, Cancer Research 58; 672-684:1998.

The amount of a botulinum toxin selected for peripheral administration to a target tissue according to the present disclosed invention can be varied based upon criteria such as the thalamically mediated disorder being treated, its severity, the extent of brain tissue involvement or to be treated, solubility characteristics of the neurotoxin toxin chosen as well as the age, sex, weight and health of the patient. For example, the extent of the area of brain tissue influenced is believed to be proportional to the volume of neurotoxin injected, while the quantity of the thalamically mediated disorder suppressant effect is, for most dose ranges, believed to be proportional to the concentration of the botulinum toxin peripherally administered. Methods for determining the appropriate route of administration and dosage are generally determined on a case by case basis by the attending physician. Such determinations are routine to one of ordinary skill in the art (see for example, *Harrison's Principles of Internal Medicine* (1998), edited by Anthony Fauci et al., 14$^{th}$ edition, published by McGraw Hill).

A dose of a non-botulinum toxin type A is an equivalent to a dose of botulinum toxin type A if they both have about the same degree of prevention or treatment when administered to a mammal (although their duration may differ). The degree of prevention or treatment may be measured by the evaluation of the improved patient function criteria set forth below.

The botulinum toxin can be peripherally administered according to the present disclosed methods in amounts of between about $10^{-4}$ U/kg to about 20 U/kg (units of type A), or an equivalent of U/kg of a non-type A botulinum toxin. A dose of about $10^{-4}$ U/kg can result in a thalamically mediated disorder suppressant effect if delivered to a small target brain nuclei. Peripheral administration of less than about $10^{-4}$ U/kg of a botulinum toxin does not result in a significant or lasting therapeutic result. A peripheral dose of more than about 20 U/kg of a botulinum toxin (such as BOTOX) poses a risk of systemic effects. Accordingly, administration of a botulinum toxin to an intracranial target tissue involved in thalamically mediated disorders through a peripheral route as set forth herein can effectively reduce symptoms associated with the thalamically mediated disorder to be treated without causing significant undesired cognitive dysfunction. Thus, the methods of the present invention can provide a more selective treatment with fewer undesirable side effects than current systemic therapeutic regimes.

In some embodiments, about 1 unit to about 40 units of botulinum toxin type A, or the equivalent of other types, are administered to a trigeminal and/or spinal nerve in accordance with the present invention. In some embodiments, about 3 units to about 30 units of botulinum toxin type A, or the equivalent of other types, are administered to a trigeminal or spinal nerve in accordance with the present invention. In some embodiments, about 5 units to about 25 units of botulinum toxin type A, or the equivalent of other types, are administered to a trigeminal or spinal nerve in accordance with the present invention. In some embodiments, about 5 units to about 15 units of botulinum toxin type A, or the equivalent of other types, are administered to a trigeminal or spinal nerve in accordance with the present invention.

In some embodiments, one or more nerve is injected with a botulinum toxin to treat a thalamically mediated disorder supra-orbital nerve (bilaterally about 5 units of type A, or the equivalent of other types, on each side), supra-trochlear nerve (about 5 units of type A, or the equivalent of other types, on each side), frontal branches of the trigeminal nerve (about 12.5 units type A, or the equivalent of other types, each side), auriculotemporal nerve (about 20 units of type A, or the equivalent of other types, on each side), lesser occipital nerve (about 5 units of type A, or the equivalent of other types, on each side), and/or greater occipital nerve (about 5 units of type A, or the equivalent of other types, on each side). In some embodiments, the total dose administered per session is about 105 units of botulinum toxin type A, or the equivalents of other types.

In some embodiments, the particular amount of a botulinum toxin administered according to a method within the scope of the disclosed invention can vary according to the particular characteristics of the thalamically mediated disorder being treated, including its severity and other various patient variables including size, weight, age, and responsiveness to therapy. As a general guide, typically, no less than about 1 unit and no more than about 50 units of a botulinum toxin type A (such as BOTOX®) is administered per injection site, per patient treatment session. For a botulinum toxin type A such as DYSPORT®, no less than about 2 units and no more about 200 units of the botulinum toxin type A are administered per administration or injection site, per patient treatment session. For a botulinum toxin type B such as MYOBLOC®, no less than about 40 units and no more about 2500 units of the botulinum toxin type B are administered per administer or injection site, per patient treatment session. Less than about 1, 2 or 40 units (of BOTOX®, DYSPORT® and MYOBLOC® respectively) can fail to achieve a desired therapeutic effect, while more than about 50, 200 or 2500 units (of BOTOX®, DYSPORT® and MYOBLOC® respectively) can result in clinically observable and undesired muscle hypotonicity, weakness and/or paralysis.

In some embodiments, for BOTOX®, no less than about 2 units and no more about 20 units of a botulinum toxin type A; for DYSPORT® no less than about 4 units and no more than about 100 units, and; for MYOBLOC®, no less than about 80 units and no more than about 1000 units are, respectively, administered per injection site, per patient treatment session.

In some embodiments, for BOTOX® no less than about 5 units and no more about 15 units of a botulinum toxin type A; for DYSPORT® no less than about 20 units and no more than about 75 units, and; for MYOBLOC®, no less than about 200 units and no more than about 750 units are, respectively, administered per injection site, per patient treatment session. It is important to note that there can be multiple injection sites (i.e. a pattern of injections) for each patient treatment session.

Significantly, a method within the scope of the present invention can provide improved patient function. "Improved patient function" can be defined as an improvement measured by factors such as a reduced pain, reduced time spent in bed, increased ambulation, healthier attitude, more varied lifestyle and/or healing permitted by normal muscle tone. Improved patient function is synonymous with an improved quality of life (QOL). QOL can be assessed using, for example, the known SF-12 or SF-36 health survey scoring procedures. SF-36 assesses a patient's physical and mental health in the eight domains of physical functioning, role limitations due to physical problems, social functioning, bodily pain, general mental health, role limitations due to emotional problems, vitality, and general health perceptions. Scores obtained can be compared to published values available for various general and patient populations.

A method for treating a thalamically mediated disorder according to the invention disclosed herein has many benefits and advantages, including the following:
1. the symptoms of a neurological disorder, such as a thalamically mediated disorder, can be dramatically reduced or eliminated.
2. the symptoms of a thalamically mediated disorder can be reduced or eliminated for at least about two weeks to about six months per injection of neurotoxin and for from about one year to about five years upon use of a controlled release neurotoxin implant.
3. few or no significant undesirable side effects occur from an intradermal or subdermal) injection or implantation of the botulinum toxin.
4. the present methods can result in the desirable side effects of greater patient mobility, a more positive attitude, and an improved quality of life.

The following non-limiting examples provide those of ordinary skill in the art with possible case scenarios and specific methods to treat conditions within the scope of the present invention and are not intended to limit the scope of the invention. In the following examples various modes of peripheral administration of a botulinum toxin can be carried out. For example, by topical application (cream or transdermal patch), subcutaneous injection, or subdermal implantation of a controlled release implant.

EXAMPLES

Example 1

Supraorbital and Supratrochlear Administration of Botulinum Toxin

The supraorbital and supratrochlear nerves innervate the frontal part of scalp and forehead. Both nerves are branches of the first division or ophthalmic branch of the trigeminal nerve. The supraorbital nerve exits the skull through the supraorbital foramen that lies in the midpupillary line, which is approximately 2.5 cm lateral to the facial midline along the supraorbital ridge. The supratrochlear nerve exits the skull along the upper medial corner of the orbit in the supratrochlear notch, which is approximately 1.5 cm medial to the supraorbital foramen.

Supraorbital and supratrochlear administration of botulinum toxin may be performed from either the area of the supraorbital foramen or the area of the supratrochlear notch. If performed from the supraorbital foramen, the area should be located, and a skin wheal raised at the site. The needle is inserted through the anesthetized area and advanced to the bone. Approximately 5 units of botulinum toxin (e.g., type A) is injected outside the foramen at the level of the inferior frontalis muscle.

The supratrochlear nerve may be reached by advancing the needle 1.5 cm medial to the junction of the supraorbital ridge and the root of the nose. As before, about 5 units of botulinum toxin (e.g., type A) is injected.

If the injection is performed from the area of the supratrochlear nerve, a wheal should be placed over the root of the nose at the junction of the nasal root and supraorbital ridge. The skin is infiltrated along the length of the entire eyebrow. When this injection is used, patients should be warned about the possibility of swelling in the upper and/or lower eyelids. For this type of injection, about 5 units of botulinum toxin (e.g., type A) per side is usually sufficient, and no more than 20 units should be injected into either side. As with any injection, the risk of ecchymosis or hematoma formation exists.

Example 2

Infraorbital Administration of Botulinum Toxin

The infraorbital nerve innervates the lower eyelid, medial aspect of the cheek, upper lip, and lateral portion of the nose. It is a branch of the second division or maxillary branch of the trigeminal nerve. The infraorbital nerve exits the skull through the infraorbital foramen, which is 1 cm inferior to the infraorbital ridge and approximately 2.5 cm lateral to the facial midline in the midpupillary line. After exiting the infraorbital foramen, the infraorbital nerve divides into 4 branches: the inferior palpebral, internal nasal, external nasal, and superior labial branches.

An infraorbital injection may be performed in 2 ways: via direct cutaneous injection or via intraoral injection. The infraorbital foramen should be palpated, and approximately 5 units of botulinum toxin (e.g., type A) is injected near, but not into, the canal to surround the nerve.

If the injection is to be performed via the intraoral approach, the application of a topical anesthetic to the mucosa before injection may increase patient comfort. The infraorbital foramen should be palpated with the middle finger of one hand while the thumb and index finger of the same hand are used to raise the lip. During palpation of the foramen, the needle is inserted into the superior labial sulcus at the apex of the canine fossa. Approximately 5 units of botulinum toxin (e.g., type A) is injected in the vicinity of the infraorbital foramen.

It is advisable to warn patients that swelling of the lower eyelid and ecchymosis may occur with the infraorbital injection. In addition, if anesthetic solution is injected into the orbit, excessive pain, diplopia, exophthalmos, and blindness can occur. The likelihood of the reactions is increased if the needle is placed superior to the infraorbital rim or into the infraorbital foramen.

Example 3

Mental Nerve Administration of a Botulinum Toxin

The mental nerve innervates the lower lip and chin. It is a branch of the third division or mandibular portion of the trigeminal nerve. The mental nerve exits the skull through the mental foramen, which is located approximately 2.5 cm from the midline of the face in the midpupillary line.

Either a cutaneous or intraoral approach can be used to inject the mental nerve. To inject the nerve cutaneously, the foramen should be palpated, and a wheal of botulinum toxin placed. Then, the needle should be reinserted and advanced to the vicinity of the mental foramen but not into it.

Approximately 5 units of botulinum toxin (e.g., type A) should be injected into the area. Alternatively, when an intraoral approach is used, the foramen should be palpated with the middle finger of one hand and the lip lifted by the thumb and index finger of the same hand. The needle should be inserted at the inferior labial sulcus at the apex of the first bicuspid and 5 units of botulinum toxin (e.g., type A) injected.

Example 4

Use of a Botulinum Toxin to Treat Epilepsy

A 23 year man can presents with chronic seizures dating from childhood. These can involve tonic clonic movements that start in the right arm and progress up the arm to the face. Eventually he can lose consciousness and have a generalized body seizure lasting about 3 minutes. His neurological examination and head MRI scan can be normal. He can be on 3 anticonvulsant medications: Depakote, Tegretol, and Topamax and he can still have seizures about once a week. The Department of Motor Vehicles (DMV) may not allow him to drive. His treatment history can include 3 courses of a botulinum toxin type A using a 4 cc dilution and injecting using the trigeminal targeting approach as follows: supra-orbital nerve bilaterally 5 units each side, supra-trochlear nerve 5 units each side, frontal branches of the trigeminal nerve 12.5 units each side, auriculotemporal nerve 20 units each side, lesser occipital nerve 5 units on each side, and greater occipital nerve 5 units on each side. Total dose can be 105 units.

In some embodiments, the referenced botulinum units are units of botulinum toxin type A. In some embodiments, the botulinum toxin employed is not type A, but would have the same unit equivalent as that of type A. His seizure control can improve 4 weeks after the first treatment and he can be currently only on Depakote, and can have been successfully weaned off of the other 2 anticonvulsants. He can be seizure free for 6 months.

Example 5

Use of a Botulinum Toxin to Treat Chronic Pain Syndrome with Central Sensitization A 60 year old woman can have a chronic history of fibromyalgia with 18 out of 18 positive tender points. Her treatment history can include tricyclic antidepressants and high doses of Neurontin. Despite these medications, she can require escalating doses of narcotics to achieve pain control. She can develop allodynia of the face, scalp, neck and shoulder girdle, as well as along her extremities. Steroid trigger point injections may not provide relief. She can experience chronic daily headache. Subsequently, she can be treated with a botulinum toxin type A, 4 cc dilution, using the trigeminal targeting approach, with 105 units at the sites outlined above. After 3 treatment cycles, her total body pain can decrease with each cycle of treatment, so that she can be currently free of headaches, and body discomfort can be is limited to the neck and jaw only. As a result of her residual discomfort the fourth treatment can involve an increased dose and increased sites of Botulinum treatment as follows: in addition to the above sites, the cervical sensory rami can be treated by infiltrating the cervical paraspinal muscles with 15 units on each side, and the masseter motor branches can be treated with 15 units on each side. The total dose given can be 165 units. She can no longer be on daily oral medications and her pain can have resolved.

Example 6

Use of a Botulinum Toxin to Treat Central Post Stroke Pain Syndrome

An 80 year old man with hypertension and diabetes can have a stroke involving the thalamus. Three months later, he can develop dysesthesias (a poorly localized burning sensation that can occur in his extremities after a stimulus is applied), hyperpathia (a heightened response to a painful stimulus) and allodynia (a non painful stimulus is felt as pain). His condition may not improve with intra venous lidocaine and large amounts of oral opioids. Amitriptyline, Tegretol and Lamotrigine can also provide no benefit. He can be treated with a botulinum Toxin Type A, 4 cc dilution, using the trigeminal targeting approach on one occasion. This can result in complete pain relief within 6 weeks of treatment.

Example 7

Use of a Botulinum Toxin to Treat Regional Pain Syndrome

A 40 year old woman can develops reflex sympathetic dystrophy of the right lower extremity following a fall with a fractured fibular that requires surgically stabilization. A trial subcutaneous injection of a botulinum toxin type A along the painful dermatomes can provide no pain relief. The patient can complain of increased leg muscle fatigue after this treatment. She can have chronic renal failure and can be resistant to using oral treatments. A trigeminal targeting approach can be utilized using the protocol established in the above cases. Once again 105 units can be injected. After 2 treatment cycles her pain can decrease to the point that she can once again start an exercise program.

Example 8

Use of a Botulinum Toxin to Treat Phantom Limb Pain

A 68 year old, diabetic woman can have had a left above knee amputation as a result of peripheral vascular disease. She can have severe residual left foot pain which keeps her awake at night. She can have tried hypnosis without benefit. She can be on Pamelor and Neurontin and can note mild benefit for sleep, but not pain. After two cycles of a trigeminal targeting of a botulinum toxin type A treatment she can be able to sleep through the night and can be in no discomfort.

Example 9

Use of a Botulinum Toxin to Treat Demyelinating Diseases

A 28 year old woman can have relapsing remitting multiple sclerosis and be on Betaseron with relapses occurring about twice a year. She can tolerate the other MS immune modulating treatments poorly. She can have had rheumatic fever as a child. Consequently, other available MS modulating treatment may not be available to her. In desperation, a botulinum toxin type A, trigeminal targeting, can be used with the standard 105 unit dose. After 4 cycles of treatment, she can have had only one relapse in the first month and her brain MRI scan can show no enhancing lesions.

Example 10

Use of a Botulinum Toxin to Treat a Bipolar Disorder

A female patient 24 years of age can experience rapid mood cycles from depression to euphoria which can require frequent admissions to psychiatric units and she is diagnosed with bipolar disorder. Thirty units of a botulinum toxin type can be administered subdermally around branches of the trigeminal nerve and cervical plexus. Specifically, one of more of the following locations can be administered (such as by injection) the botulinum toxin: (1) the frontal branch of the ophthalmic division of the trigeminal nerve divides in the orbit into the supratrochlear nerve and the supraorbital nerve. The supratrochlear nerve exits the orbit between the trochlea and the supraorbital foramen. The supraorbital nerve exits from the superior aspect of the orbit passing through the supraorbital foramen. The supratrochlear and supraorbital nerve branches of the trigeminal nerve can be localized for administration of a botulinum toxin thereto by the supraorbital foramen or notch. Both of these nerves then travel under the frontalis muscle and above the periosteum. Thus, a botulinum toxin can be administered below the frontalis muscle and above the periosteum to infiltrate these peripheral branches (supratrochlear and supraorbital nerves) of the trigeminal nerve. (2) The auriculotemporal branch of the trigeminal nerve arises from the mandibular division of the trigeminal nerve and exits in the region of the temporomandibular joint at which location the botulinum toxin can be administered. (3) The superficial temporal branches of the trigeminal nerve accompany the superficial temporal artery which is easily palpated for administration of a botulinum toxin along its course. (4) The cervical rami of the trigeminal give rise to the greater and lesser occipital nerves to which a botulinum toxin can be administered at the location where they cross the nuchal ridge just medial and lateral to the palpable occipital artery which lies midway between the mastoid process and the inion. (5 The rami of the lower cervical nerves of the trigeminal nerve can be infiltrated with a botulinum toxin at the location where they penetrate the semispinalis muscle and trapezius muscle. Thus, administration of the botulinum toxin can be, for example, to one or more of these five trigeminal nerve branch sites. After treatment, the patients' bipolar condition can improve within several weeks.

Example 11

Use of a Botulinum Toxin to Treat a Pain

The patient can be a woman in her 30's with reflex sympathetic dystrophy affecting the right lower extremity status post an ankle fracture 5 years earlier. The pain can be intractable to medical therapy including botulinum toxin type A injections to the painful dermatomes. However following botulinum toxin type A injections to the trigeminal and cervical plexus sensory branches (as set forth by Example 10), her pain can gradually diminish, and by the fourth, three monthly cycle, she can be weaned off all medical treatments and can function normally.

Example 12

Use of a Botulinum Toxin to Treat a Epilepsy

The patient can be a 48 year old male with partial sensory seizures that secondarily generalize. He can have frequent generalized tonic clonic seizures with a poor response to medical treatment. Vagal nerve stimulator (VNS) can be considered as this has been approved for partial onset seizures. The presumed mechanism of action of VNS is that cortical afferents can be down regulated via stimulation of the vagal nerve. However, VNS may worsen sleep apnea, and as this can be an issue in this patient, VNS can be replaced by botulinum toxin type A injections around sensory branches of the trigeminal nerve and cervical plexus, as set forth in Example 10 above. After two treatment cycles, the patients seizures can be controlled with standard oral anticonvulsants for the first time. The injection technique used can involve branches of the trigeminal nerve and cervical plexus such that cosmesis can be spared, i.e. lower facial and limb muscle strength can be preserved using this technique.

Example 13

Treatment of Schizophrenia with Botulinum Toxin Type A

A 48 year old male can present with reduced motivation and interest in daily life. The patient can indicate that he hears voices. The patient can be monitored regularly for six months. The symptoms can gradually worsen throughout the monitoring period, and the patient can be diagnosed with schizophrenia. Thirty units of a botulinum toxin type can be administered subdermally around branches of the trigeminal nerve and cervical plexus, as set forth by Example 10. The patient can be discharged within 48 hours and within a few (1-7) days can enjoy a significant improvement of (relief from) the positive symptoms of schizophrenia. The positive symptoms of schizophrenia can remain significantly alleviated for between about 2 to about 6 months. For extended therapeutic relief, one or more polymeric implants incorporating a suitable quantity of a botulinum toxin, such as a botulinum toxin type A can be placed at the target tissue site.

Example 14

Treatment of Schizophrenia with Botulinum Toxin Type B

A 68 year female previously diagnosed and treated for schizophrenia can wish to try a new therapeutic treatment. She can seek the advice of a physician who can recommend botulinum toxin therapy. From 200 to about 2000 units of a botulinum toxin type B preparation (such as Neurobloc® or Innervate™) can be administered to the pedunculopontine nuclei by subdermal injection of the botulinum toxin around branches of the trigeminal nerve and cervical plexus, as set forth by Example 10. The patient can be discharged within 48 hours and within a few (1-7) days can enjoy significant improvement of the positive symptoms of schizophrenia. Her hallucinations can almost completely disappear. The positive symptoms can remain significantly alleviated for between about 2 to about 6 months. For extended therapeutic relief, one or more polymeric implants incorporating a suitable quantity of a botulinum toxin type B can be placed at the target tissue site.

Example 15

Treatment of Schizophrenia with Botulinum Toxin Types $C_1$-G

A female aged 71 can be admitted with disordered thought patterns and suffering from auditory and visual hallucinations. From 1 to 100 units of a botulinum toxin type $C_1$, D, E, F or G can be administered to the pedunculopontine nuclei, by subdermal injection around branches of the trigeminal nerve and cervical plexus, as set forth by Example 10, to chemically denervate the excitatory cholinergic projection to the ventral tegmental area. The patient can be discharged within about 48 hours and with a few (1-7) days enjoys significant remission of all hallucinations which can remain significantly alleviated of the symptoms of schizophrenia for between about 2 to about 6 months. For extended therapeutic relief, one or more polymeric implants incorporating a suitable quantity of a botulinum toxin type $C_1$, D, E, F or G can be placed at the target tissue site.

Example 16

Treatment of Alzheimer's Disease with Botulinum Toxin Type A

An 85 year old male who has experienced a progressive decline in mental acuity and who no longer remembers how to perform simple tasks, such as brushing teeth, or combing hair can be admitted. The patient can be otherwise healthy for an 85 year old. He can be diagnosed with advanced Alzheimer's disease. About thirty units of a botulinum toxin type A can be administered to his locus coeruleus by subdermal injection of the botulinum toxin around branches of the trigeminal nerve and cervical plexus, as set forth by Example 10.

Although the patient's loss of memory may not recover fully, the psychotic symptoms the patient was exhibiting can be reduced and can remain substantially alleviated for between about 2 months to about 6 months per toxin injection or for between about 1 to 5 years depending upon the particular release characteristics of the implant polymer and the quantity of botulinum toxin loaded therein.

Example 17

Treatment of Alzheimer's Disease with Botulinum Toxin Types B-G

The patient of Example 16 above can be equivalently treated using the same protocol and, as set forth by Example 10 with between about 1 unit and about 1000 units of a botulinum toxin type B, $C_1$, D, E, F or G in aqueous solution or in the form of a suitable subdermal neurotoxin implant. With such a treatment, the psychotic symptoms can subside within 1-7 days, and can remain substantially alleviated for between about 2-6 months per toxin injection or for between about 1 to 5 years depending upon the particular release characteristics of the implant polymer and the quantity of neurotoxin loaded therein.

Example 18

Treatment of Mania with Botulinum Toxin Type A

A 44 year old male can be diagnosed with mania. Thirty units of a botulinum toxin type A can be subdermally, non-intramuscularly injected around branches of the trigeminal nerve and cervical plexus, as set forth by Example 10. The patients manic symptoms can subside within 1-7 days, and can remain substantially alleviated for between about 2 months to about 6 months per toxin injection or for between about 1 to 5 years depending upon the particular release characteristics of an implant polymer which can be inserted and the quantity of the botulinum toxin loaded therein. Notably, there can be significant attenuation of the manic behavior and the patient has a substantially more controlled behavioral pattern.

Example 19

Treatment of Mania with Botulinum Toxin Types B-G

The patient of example 18 above can be equivalently treated using the same protocol and approach to target with between about 1 unit and about 1000 units of a botulinum toxin type B, $C_1$, D, E, F or G in aqueous solution or in the form of a suitable neurotoxin implant. With such a treatment, the symptoms can subside within 1-7 days, and can remain substantially alleviated for between about 2-6 months per toxin injection or for between about 1 to 5 years depending upon the particular release characteristics of the implant polymer and the quantity of neurotoxin loaded therein. The implant can be implanted at one or more of the locations specified in Example 10.

Example 20

Treatment of Epilepsy with Botulinum Toxin Type A

A right handed, female patient age 22 can present with a history of epilepsy. Based upon MRI and a study of EEG recording, a diagnosis of temporal lobe epilepsy can be made. An implant which provides about 5-50 units of a neurotoxin (such as a botulinum toxin type A) can be inserted subdermally around branches of the trigeminal nerve and cervical plexus, as set forth by Example 10. The epileptic seizures can be substantially reduced within about two weeks, and can remain substantially alleviated for between about 2 months to about 6 months per toxin injection or for between about 1 to 5 years depending upon the particular release characteristics of the implant polymer and the quantity of a botulinum toxin loaded therein.

Example 21

Treatment of Epilepsy with Botulinum Toxin Types B-G

The patient of example 20 above can be equivalently treated using the same protocol and approach to target with between about 1 unit and about 1000 units of a botulinum toxin type B, $C_1$, D, E, F or G in aqueous solution or in the form of a suitable neurotoxin implant. The implant can be implanted at one or more of the locations specified in Example 10. With such a treatment, the epileptic seizures can subside within 1-7 days, and can remain substantially alleviated for between about 2-6 months per toxin injection or for between about 1 to 5 years depending upon the particular release characteristics of the implant polymer and the quantity of neurotoxin loaded therein.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety. All references, articles, patents, applications and publications set forth above are incorporated herein by reference in their entireties.

I claim:

1. A method for treating a post-traumatic stress disorder in a patient in need thereof, comprising directly administering a botulinum toxin to a trigeminal nerve of the patient, thereby treating the post-traumatic stress disorder.

2. The method of claim 1, wherein the botulinum toxin is botulinum toxin type A.

3. The method of claim 1, wherein the botulinum toxin is botulinum toxin type B.

4. The method of claim 1, wherein the method of local administration is injection.

5. The method of claim 1, wherein the administering is by non-intramuscular injection.

6. The method of claim 1, wherein the administering is subdermal, intradermal or transdermal.

7. The method of claim 1, wherein the trigeminal nerve is selected from the group consisting of an ophthalmic nerve, maxillary nerve, mandibular nerve, supra orbital nerve, supra trochlear nerve, infraorbital nerve, lacrimal nerve, nasociliary nerve, superior alveolar nerve, buccal nerve, lingual nerve, inferior alveolar nerve, mental nerve, an auriculotemporal nerve, lesser occipital nerve and a greater occipital nerve.

8. A method for reducing the occurrence of a symptom of post-traumatic stress disorder in a patient with post-traumatic stress disorder, the method comprising locally administering a therapeutically effective amount of a botulinum toxin to a trigeminal sensory nerve or to the vicinity of a trigeminal sensory nerve of the patient, thereby reducing the occurrence of a symptom of post-traumatic stress disorder, wherein the administering is non-intramuscular.

9. The method of claim 8, wherein the botulinum toxin is botulinum toxin type A.

10. The method of claim 8, wherein the botulinum toxin is botulinum toxin type B.

11. The method of claim 8, wherein the method of local administration is injection.

12. The method of claim 8, wherein the administering is by subdermal, intradermal or transdermal.

13. The method of claim 8, wherein the administering is subdermal.

14. The method of claim 8, wherein the therapeutically effective amount of the botulinum toxin administered is between about 1 unit and about 3,000 units.

15. The method of claim 8, wherein the trigeminal sensory nerve is selected from the group consisting of an ophthalmic nerve, maxillary nerve, mandibular nerve, supra orbital nerve, supra trochlear nerve, infraorbital nerve, lacrimal nerve, nasociliary nerve, superior alveolar nerve, buccal nerve, lingual nerve, inferior alveolar nerve, mental nerve, an auriculotemporal nerve, lesser occipital nerve and a greater occipital nerve.

* * * * *